(12) United States Patent
Szyf et al.

(10) Patent No.: US 6,221,849 B1
(45) Date of Patent: *Apr. 24, 2001

(54) DNA METHYLTRANSFERASE GENOMIC SEQUENCES AND ANTISENSE OLIGONUCLEOTIDES

(75) Inventors: Moshe Szyf, Cote St. Luc (CA); Pascal Bigey, Clermont-Ferrand (FR); Shyam Ramchandani, Montreal (CA)

(73) Assignee: MethylGene, Inc., Quebec (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/103,875

(22) Filed: Jun. 24, 1998

Related U.S. Application Data

(63) Continuation-in-part of application No. 08/866,340, filed on May 30, 1997, now Pat. No. 6,020,318
(60) Provisional application No. 60/069,865, filed on Dec. 17, 1997.

(51) Int. Cl.$^7$ .................. A61K 31/7088; A61K 31/712; A61K 31/7125; C07H 21/04

(52) U.S. Cl. ..................... 514/44; 435/375; 536/24.5

(58) Field of Search .................. 435/6, 194, 375; 514/44; 536/24.3, 24.31, 24.5

(56) References Cited

U.S. PATENT DOCUMENTS

| | | | |
|---|---|---|---|
| 5,578,716 | 11/1996 | Szyf et al. | 536/24.5 |
| 5,585,479 | 12/1996 | Hoke et al. | 536/24.5 |
| 5,919,772 | * 7/1999 | Szyf et al. | 514/44 |
| 6,020,318 | * 2/2000 | Szyf et al. | 514/44 |

FOREIGN PATENT DOCUMENTS

95/15378  6/1995 (WO).

OTHER PUBLICATIONS

Citti et al. (1994) The genotoxicity of chlorethylating agent mitozolomide is enhanced in CHO mex+ cells by the administration of antisense oligonucleotide . . . Anticancer Res. 14:2667–2672.*
"Antisense '97: a roundtable on the state of the industry." *Nat. Biotechnol.* . . 15(6):519–524 (1997).
Agrawal. S. "Antisense oligonucleotides as antiviral agents." *Trends in Biotech* 10:152–158 (1992).
Bartolomei et al., "Epigenetic mechanisms underlying the imprinting of the mouse H19 gene." *Genes Dev.* 7:1663–1673 (1993).
Burch and Mahan, "Oligonucleotides antisense to the interleukin 1 receptor mRNA block the effects of interleukin 1 in cultured murine and human fibroblasts and in mice," *J. Clin. Invest.* 88:1190–1196 (1991).
Brandeis et al., "The ontogeny of allele–specific methylation associated with imprinted genes in the mouse." *EMBO J.* 12:3669–3677 (1993).

Feinberg and Vogelstein, "Hypomethylation distinguishes genes of some human cancers from their normal counterparts." *Nature* 301:89–92 (1983).
Feinberg et al., "Reduced genomic 5–methylcytosine content in human colonic neoplasia." *Can. Res.* 48:1159–1161 (1988).
Freedman et al., "Cellular tumorigenicity in nude mice: correlation with cell growth in semi–solid medium.." *Cell* 3:355–359 (1974).
Gewirtz et al., "Facilitating oligonucleotide delivery: helping antisense deliver on its promise." *Proc. Natl. Acad. Sci. USA* 93(8):3161–3163 (1996).
Goelz et al., "Hypomethylation of DNA from benign and malignant human colon neoplasms." *Science* 228:187–190 (1985).
Gura, T. "Antisense has growing pains." *Science* 270(5236):575–577 (1995).
Holliday, R. "DNA methylation and epigenetic inheritance." *Philos Trans. R. Soc. Lond. B. Biol. Sci.* 326:329–338 (1990).
Ingraham et al., "A family of POU–domain and Pit–1 tissue–specific transcription factors in pituitary and neuroendocrine development." *Annual Review of Physiology* 52:773–791 (1990).
Jones et al., "The role of DNA methylation in cancer." *Adv. in Cancer Res.* 54:1–23 (1990).
Leonetti et al., "Antiviral activity of conjugates between poly(L–lysine) and synthetic oligodeoxyribonucleotides." *Gene* 72:323–332 (1988).
Lock et al., "Methylation of the Hprt gene on the inactive X occurs after chromosome inactivation." *Cell* 48:39–46 (1987).
MacLeod and Szyf, "Expression of antisense to DNA methyltransferase mRNA induces DNA demethylation and inhibits tumorigenesis." *J. Biol. Chem.* 270(14):8037–8043 (1995).
Maniatis et al., "Regulation of inducible and tissue–specific gene expression." *Science* 236:1237–1245 (1987).
Meyer et al., "A derivative of staurosporine (CGP 41 251) shows selectivity for protein kinase C inhibition and in vitro anti–proliferative as well as in vivo anti–tumor activity." *Int. J. Cancer* 43:851–856 (1989).

(List continued on next page.)

*Primary Examiner*—Robert A. Schwartzman
*Assistant Examiner*—Thomas G. Larson
(74) *Attorney, Agent, or Firm*—Hale and Dorr LLP

(57) ABSTRACT

The invention provides recombinant nucleic acids comprising nucleic acid sequences from the genomic DNA methyltransferase gene. The invention further provides sequence information for such nucleic acid sequences. In addition, the invention provides antisense oligonucleotides complementary to special regions of the genomic DNA methyltransferase gene or its RNA transcript. Finally, the invention provides methods for using such antisense oligonucleotides as analytical and diagnostic tools, as potentiators of transgenic plant and animal studies and gene therapy approaches, and as potential therapeutic agents.

8 Claims, 14 Drawing Sheets

OTHER PUBLICATIONS

Migeon, B.R., "X–chromosome inactivation: molecular mechanisms and genetic consequences." *Trends Genet.* 10:230–235 (1994).

Ohtani–Fujita et al., "CpG methylation inactivates the promoter activity of the human retinoblastoma tumor–suppressor gene." *Oncogene* 8:1063–1067 (1993).

Peterson et al., "Imprinting the genome: imprinted genes, imprinting genes, and a hypothesis for their interaction." *Ann. Rev. Genet.* 27:7–31 (1993).

Pon, R.T., "Solid–phase supports for oligonucleotides synthesis." *Methods in Molecular Biology* 20:465–496 (1993).

Ramchandani S. et al., "Inhibition of tumorigenesis by a cytosine–DNA, methyltransferase, antisense oligodeoxynucleotide." *Proc. Natl. Acad. Sci. USA* 94(2):684–689 (1997).

Ramchandani S. et al., "Genomic structure of the human DNA methyltransferase gene." *Biol. Chem.* 379(4–5):535–540 (1998).

Rojanasakul, "Antisense oligonucleotide therapeutics: Drug delivery and targeting," *Adv. Drug Delivery Rev.* 118:115–131 (1996).

Stepheneson et al., "Inhibition of Rous sarcoma viral RNA translation by a specific oligodeoxyribonucleotide." *Proc. Natl. Acad. Sci. U.S.A.* 75:285–288 (1978).

Stull et al., "Antigene, ribozyme and aptamer nucleic acid drugs: progress and prospects." *Pharm. Res.* 12(4):465–483 (1995).

Szyf et al., "Nucleotide–sequence–specific de novo methylation in a somatic murine cell line." *Proc. Natl. Acad. Sci. USA* 86:6853–6857 (1989).

Szyf et al., "Ras induces a general DNA demethylation activity in mouse embryonal P19 cells." *J. Biol. Chem.* 270:12690–12696 (1995).

Szyf et al., "Growth regulation of mouse DNA methyltransferase gene expression." *J. Biol. Chem.* 266:10027–10030 (1991).

Szyf et al., "Cell cycle–dependent regulation of eukaryotic DNA methylase level." *J. Biol. Chem.* 260:8653–8656 (1985).

Szyf et al., "Induction of myogenic differentiation by an expression vector encoding the DNA methyltransferase cDNA sequence in the antisense orientation." *J. Biol. Chem.* 267:12831–12836 (1992).

Szyf, M. "The DNA methylation machinery as a target for anticancer therapy." *Pharmacol. Ther.* 70(1):1–37 (1996).

Szyf et al., "cis modification of the steroid 21–hydroxylase gene prevents its expression in the Y1 mouse adrenocortical tumor cell line." *Mol. Endocrin.* 4:1144–1152 (1990).

Yen R.–W. C. et al., "Isolation and characterization of the cDNA encoding human DNA methyltransferase." *Nucleic Acids Res.* 20(9):2287–2291 (1992).

Yoder J. A. et al., "New 5' regions of the murine and human genes for DNA (cytosine–5)–methyltransferase." *J. Biol. Chem.* 271(49):31092–31097 (1996).

Yoder and Bestor, "Genetic analysis of genomic methylation patterns in plants and mammals." *Biol. Chem.* 377(10):605–610 (1996).

Zakut–Houri et al., "A single gene and a pseudogene for the cellular tumour antigen p653." *Nature* 306:594–597 (1983).

Zhao Q. et al., "Effect of different chemically modified oligodeoxynucleotides on immune stimulation." *Biochem. Pharmacol.* 51(2):173–182 (1996).

Zon et al., "Phosphorothioate oligonucleotides" *Oligonucleotides and Analogues: A Practical Approach*, Eckstein, eds. IRL Press, New York, pp. 87–108 (1991).

* cited by examiner

FIG. 1A

5TCGGGGCAGGGTGGCGGGGGTAGGAGGCAGCGCCGAGCGGCTGGCTGGAAGAGAGTGT
SEQ ID NO 1
GGTGTGTCGGACGGGCAGCTTCCTGTGTGCTCCAAGGGATGAGCCTCGTCGGGCGnnnnnT
SEQ ID NO 2
TTCCCCATGTTTTCTTCTAGGAGCACTATAGTTTCAGGTCTTATGTTTAATCTTTAATAAGTTTTGTGTTTT
TGTATATGGTGTAAGGTAAGGGTCCAACTTCATTCTTTTGTATGTGGTTATACAGTTTTCTCAGCACCAT
TGTTAAAGACACAATCTTTCCCCCATGTTCTGGTGCTTTAAAAAAAAAAAAAAATCCTGGCTGGTTACGG
TGGCTTAGGCCTATAATCCCAGCACTTTGGGAGGCTGAGGCAAGTGGACTGCTTGAGGCTAGGAGTCCC
AGACTAGCCTGGCCAACATGGTGAAACCCTGTCTCTACCACCGAAGATACAAAAATTAGCCAGGCGTG
GTGGAGTACGCCTGTAATCCCAGCCTACTAGGGAGGCTGAGGCATGAGAATCGCTTGAACCTGGGAGG
CAGAGGTTGCAGTGAGCCAAGATCTCACCACTGCACGCCAGCCGGGGTGACAGAGTGAGGCAGGGTCT
TACCCTGTCGCCCAGGCAGGAGTCCAGTGGCCCAATCATGGCTCATTGCAGCCTACACTGCCAGGGTT
CAAGCCATCCTCCCACCTCAGCCTCCCAAGTAGCTAGGATTACAGGTGTGTGTCACCATCCCAGCAAA
TCTTGTATTTTTGTAGAGATGGGTATCCCTATGTTGCTCAGGCTGGTCTTGAACTCCTAACCTCAAGCGA
TCCTCCCACCTGGGCCTCTCAAAGCACTGGGTACAGGCGTGAGCCACTGCGCCTGACATGGTGCTTCTT
AATTTATTCTTACTTTTTATTTTTATTTTTTTGAGACAAGGTCTTGCTCTGTCTCCCAGGCTGGAATGTAG
TGGTACAATCATGGCTCACTGCAACCTCTGCCTCTCCGGTTCAAGTGATCTTCCTGCCTCAACCTCTGG
AGTAGTTTGGACTATGGGCACATGCCACAACGACTAGCTAATTTTTGTTTTTCTTTTTTTCTTTCTTTCTT
TCTTTCTTTCTTTTTTTTTTTTTTGAGATGCAGTTTCTCTATGTTACCTAGGCTGGTCTAAAACTCCTGGG
CTCAAGCGATCCTCCCACCCTGGCCTCCCAAAGTGCTGGGATGACAGGCGTGAGCCACGTGGTGCTTA
AAAAAGGCAACAAAAAACCCCCCACACACTGGGTATAGAAGTGGCATGGGGCCTCTATACACTGTGAG
ATTCTTGGTACTAGCTACAAATTCTGTGTATACTCAAGATTTTCTAGAGTAGGTGGCAATTACCCCGTTT
TACAGATGAGGACACAGAGGCTGAGCCGTAGTGACCCACCTAAGGTCGTATAGCCAGCAAATAGATGG
AGGTTGGATTGGAAACTGACAAACTGAGGACTTTACTCAAGGGCTCTCACAACCCTTGGGGGGCTTCTCGCTGCTTT
ATCCCCATCACACCTGAAAGAATGAATGAATGAATGCCTCGGGCACCGTGCCCACCTCCCAGGAAACG
TGGAGCTTGGACGAGCCCACT**CGTCCGCGTGGGGGGGGTGTGTGCCCGCCTTGCGCATGCGT
GTTCCCTGGGCATGGCCGGCTCCGTTCCATCCTTCTGCACAGGGTATCGCCTCTCTCCGT
TTGGTACATCCCCTCCTCCCCCACGCCCGGACTGGGGTGGTAGACGCGCCTCCGCTCATC
GCCCCTCCCCATCGGTTTCCGCGCGAAAAGCCGGGGCGCCTGCGCTGCCGCCGCCGCGT
CTGCTGAAGCCTCCGAGATGCCGGCGCGTACCGCCCCAGCCCGGGTGCCCACACTGGCC
GTCCCGGCCATCTCGCTGCCCGACGATGTCCGCAGGCGGTAG**GTACCATGGGGGGGAACACG
GACTCAGGGGGACAGGCAGGGCGCTGGGTGGGGGGTCGCTTCCCCTCGGGGTGGCCGGTGGCGCTGCT
GACAGACGGGCGCGCATGGCTGGGGTGGTGCGGCGCGCAGCGCAGTTGGCGCGGGCAGGGTGGCACTT

FIG. 1B

CCGGTCGCGCGTGCCCGGGCTGTTTGGGGCCAAAATGGACCGTGGATTCCCCCGTAGCTCCCTT
                                    SEQ ID NO 2 ←┐  ┌→SEQ ID NO 3
CTAGAAACTAGGCGGGGTGGGCCTCTCTTTTGATCCCCAAATACAGCnnnnnAGGAGGTCTTGCCTC
AAACTTGCCGGCTTAAAGGACATACATTTATTACCTTATGTCCAGGGTCAGAAATCTGATGC
SEQ ID NO 3 ←┐   ┌→SEQ ID NO 4
GGGTTTCACCnnnnnTCTAGAGCTCGCGGCCGCGACGTCAATTAACCCTCACTAAAGGGAGTCGACTCG
ATCGCCCTATGTTGTCCAGGGCTGGACTCGAACTCCTGCCCACAAGCCATCCTCCCACCACAGCCTCC
TGAGTAGCTGGGGTTACAGGCACGCAGCACCGCGGCACTGCACCGGCTTTTGTTCTTTTATTTTTTCCC
TCTTTGTCCCTGAAAGAGTCAAGCTACTAATTGTCAGTAATCAAATCAGACCACGATTTCCCAGGCAAA
CTCCTGGCAGTTCTACATTTAGGAATGACTAGCTAGAGACATCCTGAAGAATGAGTTATTCGGGGAGGC
GCCACGACCTCCTCTAACTTCACCTCTATCTGCCCTCTGTGTGGGTACCCCTTGCTTCCCTGGATGCTTG
ACTCCCCCATTTCATCCTCAAAATGCCACCACCCCCACCAGGCCTTTAGGAACATCAGCTGGCTGTTC
CCCACAGTGTCCTGTGGCCCTGGGCTACTCATTCTGACACTGGCCATACTGTGGCACACCTTGTTATGG
GCTGTTGTCAGACCCAACTGGAGAAAGACCAGCTGTAGGTCATTTCCCTTACGGGAGTGCCCCAACTAT
ATGACCTGCCCCCTCTTTCCTGGTATCTTTTGAGTCAGGGTCTCACTCTGTCTCCTAGATTGGAGTGCA
GTGATGCAATCACGGCTCACTGTGGCCTCGACCTCCCAGGCTCAGGTGATCTTCTTCTCAGCCTCCCAA
GTAACTGGGACCACAAGCACATGCCACCAAACCCAGTTATTTTTATTTTTATTTTATTTTATTTTGA
GACAGAGTTTCACTCTTGTTGCCCAGGCTAGAGTGCAATGGTGTGACCAGCTCACTGCAACCTCTGCCT
CCCGGGTTCAAGTGATTCTCCTGCTCAGCCTCCAAGTTGCTGGGATTACAGCCACCCACCACCCACGC
CTGGCTAATTTTTGTATTTTTAGTAGAGATGGGGTTTCGCCATGTTGGCCAGGCTGGTCTCAAACCCTTG
ACCTCAGGTAATCCACCCACCTTGGCCCTCAGGTAATCCACCCAACTGCTGCTGTATGTTGGGATTCCA
GGCATCAGCCACCACGCCCAGCCACTAATTTTTGTATTTTTGTAGAGATGGAGTTTCGCCATGTTCCCA
GGCTGGTCTGAACGCCTGGGCTCAAGTGATCCGCTCGCCTTGGCCTCCCAAAGAGCTGGGATTATAAGC
GTGAGCCACCATGCCTGGTCTCTGGTACCTTTTAAAATATACAGGCTGGGCATGATGGCTCATGCCTGT
AATCCCAGCACTTTGGGAGGCTGAGGCAGGTGGATCGCCTGAGGTCGGGAGTTCGAAACCTAGCCTGA
CCAACACGGAGAAACCCTGTCTCTGCTAAAAATATAAAATTAGCTGGGTGATGGTGGTGCATGCCTGTA
ATCCAGCTACTCGGGAGGCTGAGCCAGGAGAATCGCTTGAACCTGGGAGTCGGAGGTTTGAGCTGAGA
TCACACCATTGCACTCCAGCCTGGGCAACAAGAGCAAAACCCTATCTCAAAAAAAAAAAATATATATA
TATATATATATATATACACAGCTATATATAGCGTATATATATACACACACATATGTATACATATAT
ACGTATGTATACACATATACGTATATATACACATATATATGTATATATACACACATATACGTGTATAT
ATATACGTGTATATATATGCATGCCAGACAAGGTGACTCATGCCTGTAATCCTAGCACTTCAGGAGA
CTGAGGCAGGCGGATTCACTTGAGGTCAGGAATCTAAGACCAGGCTTAACCAACATGGTGAAACCCTG
TCTCTACTCAAAATACAAAAAATTAACGAGGCTGGTGGCACCTATAATCCCAGCTACTTGGGAGGGCTG

FIG. 1C

AGGTGAGAGAATCACTTGAACCCAGAAGGTGAGGGTTGCAGTGAGCTGAGATCGCACCACACCACTCC
ACCTGGGCAACAGAGCGAGACTCCATGTCTGTCTGTCTGTCTATCTATCTGTATAATGTATATGTATG
TGTATATATGTGTGTGTATATATATACACATATATACATACATATATACACACATACTCTGTTACAGAGC
TGCTGTGTGTGTGTATATATATATACACATATCTATATATACACATATACACATATATATGTATATATA
TACACACATATATATACACATATATATGTATATATATACACACATATATATACACATATATATGATATAT
ATACACATATATATGTATATATATACACACACACACATACACATAATTGTGTTACAGAGCTGCTATG
TAATCTCACAATCATCAGAAAAATGACCCCCAAAAGGGGAACCTTGTTCAGATCAGATGACTTCTTAGC
ATTAGGCATTCCAGTAGGACACTCTAGACTCTTGCGGGGAGACAAAAGCCAGCTTAGTTTTTTCTAACA
CTCATATGTTAAACTTGTTTGTGTCCAAAACTTCTTTAGAACTGTGATATTCTTACAGGCAAATGAAGTT
GCTTAACAAGTGTTTGTATTTTCTCCCTATTTCTTCCTCCAGG$_{78}$CTCAAAGATTTGGAAAGAGACA
GCTTAACAGAAAAG$_{114}$GTAATCTCCTCCTTAAAATTTTTCTTATTACCAAATCTGACTGACACACTT
TGTGGCTCATAAAAAGAAATTTGTTTTCTTTAAATGGATTTTGCATTTTTTCCCATGGAGTTTCAAAGATA
ATTTGGATATTCTTGTTAAATGTCAGCACTAATTTGCTGCTAATAGTTGGGTGGTGGTGGTGTTTTTTTT
GTTGTTGTTTTTGTTTTTTGAGACAGAGTCTCACTCTGTCACCCAGGCTAGAGTGCAATGGCATGATCTC
GGCCTCACTGTGACCTCTGCCTCCCGGATTCAAGCTGTTCTCCTGCCTCAGCCTCCCAAGTAGCTGGGA
CTACAGGCACGCACCACCATGCCCAGCTAATTTTTATATTATTAGTAGAGATGGGGTTTACCATGTTGG
CCAGACTGGTCTTGAACGCCTGCTCGTGATCTGCCCACCTTGGCCTCCCAAAGTGCTGGAATTACAGGC
GTGACGACCATGCCTGGCCCAGGTTTTTTTTTTTTTAACCAATCTCAGTTCCTAAACAACTCTACTCTG
GATTGTAACTTGTCCTGGTAACACTGTTTTATTGTGTTTTTGTTATTGTTTTGAGATAGGGCTCTCATTCT
GTAGCCCAGGCTGGAGTGCAGTGGCACAATTTTGGCTCACTGCAACCTTCGCCTCCCAGGCTCAAGTGA
TTTTCCCACTCAGCCTCCTGAGTAGCTCTAACTACAGGCTCAAGCCACCATGCCCAGCTAATTTTTAAA
TATTTTTTGTAAAGATGGGATTTTGTCATGTTGCCCCAGGCTGGTCTTGAACTCTGGGGCTCAAAGCAAT
CCACTTGCCTCGGCCTCCCAAAGTGCTGGGATTATAGGTGTGAGCCACTGTGCCTGGGCCGACACTTTA
CAGAAGCACAGTATTATTCTTATAAACCATGATATGTCTCCATCTCACCTCCAGCTTTCCCATTTTTCAC
CACTTTGGAGACAGGAGTGAAGTGATCCTAATGGAAATTCCCTGAACACATTTCATGACTGTTTAGTGTT
TTGACTGAGACAGCATTGCCTGCCATTCACTCATTGTGATGTGATCAGGCAGCTCAATAATTTGTGTATT
AGTCCACTAGTGAATAGCTTGGGAATGTGGGTACTGCTAAACCTATATCCTTCCCTTAGG$_{115}$AATGTG
TGAAGGAGAAATTGAATCTCTTGCACGAATTTCTGCAAACAGAAATAAAGAATCAGTTAT
GTGACTTGGAAACCAAATTACGTAAAGAAGAATTATCCGAG$_{222}$GTAAGTCAGTTCTCAGCAT
                                         OLIGO 39
CCTAGC$_{CTCTAGAA}$AAATGTCTCCTCCTAGTAACTTGTCTGTGACCAGGGAGGCAGCAAGATCCCCAGC
TGTCCTCATTGCCTGATGATGATGATGATGATGATGATGATGATGAAGAACACATGTGTTCTGTCTCTGACAC

FIG. 1D

GTGTTACATTCACTGCTACTAATTATCCTGTCCTGCTGTAGG$_{223}$AGGGCTACCTGGCTAAAGTCA

AATCCCTGTTAATAAAGATTTTGTCCTTGAGAACGGTGCTCATGCTTACAACCGGAAGTG

AATGGACGTCTAGAAAACGGGAACCAAGCAAGAAGTGAAGCCCGTAGAGTGGGAATGGC

AGATGCCAACAGCCCCCCCAAACCCCTTTCCAAACCTCGCACGCCCAGGAGGAGCAAGT

CCGATGGAGAGGCTAAGC$_{442}$GTAAGAGCAGATGATTCCTTTTATTTTTAATTGTTTTTGAGATGGAG
          OLIGO 63

TCTCACTGTGTTGCCCAGTCTGGAGCACAGTGGTGTAACCTCGGCTCACTGTAACCTCTGCCTCCAGGT
                    SEQ ID NO 4 ←       → SEQ ID NO 5

TCAAGAGACCCTCCTGCCTCAGCCTCCCAAGTAACTGnnn~600bpnnnGCCAACATTAGCAAGCTG

GTTGTTGACTAGAATAAAAATGCAAAGATGCTAGTCCTTAGAACCTGGGCTTCCTGCAATAGCTTAGTA

ATGTTGAACTGCATTATTGCTGTGGGCTTTCTATTGATAGTGGCTTTTTTTTTCTTTTTAATGCTTTTTCT

TCTTTAAACAGC$_{443}$TGAACCTTCACCTAGCCCCAGGATTACAAGGAAAAGCACCAGGCAA
        OLIGO 64

ACCACCATCACATCTCATTTTGCAAAGG$_{518}$GCTAGTATACGATAAATTGGCGGCTGCCTTTTTT
                                   SEQ ID NO 5 ←

AGGGGCCGGCTGTTTGGGATGGAATTGGTAGGGCGTCACGTGGCAATTCTGTCTTCCGTGTTGTATAnn
  → SEQ ID NO 6

1000bp~nnnTCTCTGACACTAGCAGCTGTTGATCGGTGTTTAGACCCGTGATTTCTTAGGACTTACA

AGATGGCAAGACAACATTCTAAACCCGTATTCAGAGAAACATTAAACTTGAAGCCTCTTTCAACATCC

TGGTGAATGAGGGTCCACTTCAGGCCAGCTGGAGGCCTAGGGTCTTGTTCCACTAATGGTTGGCCTCAC

TGTGTGTGACAGC$_{519}$CCTGCCAAACGGAAACCTCAGGAAGAGTCTGAAAGAGCCAAATCG
        OLIGO 65

GATGAGTCCATCAAGGAAGAAGACAAAGACCAG$_{597}$GTAGGGCCAGTGCTTTCATTTCCTGACT
                          OLIGO 66

CTACCTTACTTGGTGTATTTGATGATTGTGACTTCATATGTGTTCTGTCCAAGTAAATAAAAACCCTGTC
                                                  SEQ ID NO 6 ←

TAGGGCTCTATTAGGGCTCTCCAGAGAGACAGGACCAATAGAATGTATATGTGTGTATCAACGTATAG
  → SEQ ID NO 7 nn~1500bp~nnnGTTTTGGGGTTGGTGGGGATTAATACCAGAGTAAGAGTTTCTCAGATCTTCTCCCC

TTTTCCCAGGCCCCTTCTTTTCCCACTCTTGCTCTAACCATGTCAAATGTGTTAATATTTCAACTCACAC

TTTTGGTGTTGACCTTCCCTTGAAACCAGTATTCTAATCTTTTTTGTTCTTCCTTCCCTCCACACAGG$_{598}$

ATGAGAAGAGACGTAGAGTTACATCCAGAGAACG$_{632}$GTAAGAATAGTTACTATACCTTTCTTTT
                         SEQ ID NO 7 ←        → SEQ ID NO 8

TGTTCTACGAGTTGTGTAATCTTGATCACAAAACTTTTTCAGAAAGTTTnn~700bP~nnCAGGGCTCCG

AGATAAGTAAGATTGCTTTTGGGGAAAAGAGGAGCTTTATGAAAACTGCTTCTTTGGGGAAGCTCCTGG

CACTCACACTTGGGGTCTGTGTTATTTTGCTTGACAGA$_{633}$GTTGCTAGACCGCTTCCTGCAGAAG
                                         OLIGO 67

AACCTGAAAGAGCAAAATCAGGAACGCGCACTGAAAAGGAAGAAGAAAGAGATGAAAAA
    SEQ ID NO 8 ←     → SEQ ID NO 9

$_{717}$GTAAAGCTCTATCACCTCTAAGnnnnTACAGGCGTGAGCTACTGTGCCCACTGGTAGACAGTCTTTA

CTCCCACCAGTGACTCTAGAATCAGTTCAGGTGTTTTATTTCCATAGGACACTTTAATAGAAAGATCCA

AACCAAATGGAAAAAATTAACTTGTCTTTTTTCCCTGCAACTTAGG$_{718}$AAGAAAAGAGACTCCGA

AGTCAAACCAAAGAACC$_{752}$GTAAGTGCAGCGAACCTGCCTTTGTGCTTTGTTGTGAAACTGAATTG

FIG. 1E

CTAACATAAGTATCTTGGTAAAATAACGGGTTGGTGTGGAACAGTGGGGGCTAATCATATGTCTCTTATG

TGGGCAAGTTCTGCTTCTGCTTGTGAAAGGTGAGACCACCCTGAAGTGAAGGCTGAAGTTAACTTTTTTAACTTTA
SEQ ID NO 9 ←┐  ┌→ SEQ ID NO 10                                    SEQ ID NO 10 ←┐

ATTTAATTTAATTTAATTTnnnnCTTCAGTTTCTGTTTGGGTGTTGGTTCTTTGGTTTGACTTCGG
  ┌→ SEQ ID NO 11 nnnn~1000bp~nnTGAGTCCTGAGTAGTAAATCGTCTGGCTTCCTGCAGTGAAGACAGGAGAGGCAG

CCTGTCCTCTGAACCTGGGGAGGAGCTTGTGTCAGCCCTTAGGAGCTGTTGGCCCCGGTGCAGGGCCCC

CCCCGAGCTGACCAGCCTGTGTGTGTGTTGTCTT<u>CTGTGACAGA</u>$_{753}$ACACCCAAACAGAAACTGA
                                      OLIGO 67

AGGAGGAGCCGGACAGAGAAGCCAGGGCAGGCGTGCAGGCTGACGAGGACGAAGATGG
SEQ ID NO 11 ←┐            ┌→ SEQ ID NO 12

AGACGAGAAA$_{840}$nnnnnnnnnn1700bpnnnnnnAGAAACTAATTTTTTCCCTTCTTTATCTCTCTACCTC

CCCCTTATTTTTCTGTCAGG$_{841}$ATGAAGAAGCACAGAAGTCAACCCAAAGATCT$_{875}$GCAA

GTGTTTAAAATGCTTGTGCTTTTGTGTCATCTGGATCAGTAGAAAGCCTGTTCTAGGCCAAGGTGTGGTG

GCTTGCACCTGTAATCCCAGCTCAAAGGGAGGCTGAGGTGGGTGAATCACCTGAGGTCAGGAGTTCGA
                                                    SEQ ID NO 12 ←┐          ┌→

GACCAGCCTAGCCTGGCCAACATGGTGGAACCCTGTCTGTACTAAAAAnnnnnnnn570bpnnnnnnnATC
SEQ ID NO 13

TTGGCTTTCCCATGGGGAGGCATTAGTTTGTCACTTTCCGTGCGAGTTGGCGATGTGGTTAGTGTTTCTA

AGCTTGCTACTTGCTGTGTATCTGTT<u>CACCCTGCAGA</u>$_{876}$GCTGCCAAACGGAGGCCCGAAGAAA
                                           OLIGO 70

AAGAACCTGAAAAAGTAAATCCACAGATTTCTGATGAAAAGACGAGGATGAAAAG$_{957}$G
                                                        SEQ ID NO 13 ←┐

TAAAGGTCTCACTTTTCTTTCTTTCTTTTTTTTTTTTTTTTTTTCCCCAAGACGGGGnnnnn350bpnnnnnn
  ┌→ SEQ ID NO 14 nnnnnnGACTATAAGATTTGTATTCTATGACTTTAGATGGTAGAGTGAGTCAGAGCTCACCTGCTGGCCC

TCTCACTGCCTCCCTCCCCTTCTCTCTGTTTTATGATAATCACTTATACAAAGTTCTTAACACCGAAGCA

CTATCTGGGAGGAAAACACTCTCTTAGCCTTTAATCCTCTTTTGTTTTCCCTGTGTAGG$_{958}$AGAAGAG

ACGAAAACGACCCCCAAAGAACC$_{992}$GTAAGAATTTATTCTTGACATTATCCAAAGCAGATGGT
SEQ ID NO 14 ←┐                ┌→ SEQ ID NO 15

AATGTTAAAATGATGGTTCTAGAACAAAnnnnn300bpnnnnnnCAACGATCTTGTGATTTTTTTTTTCCC

CCAGA$_{993}$ACGGAGAAAAAAATGGCTCGCGCCAAAACAGTCATGAACTCCAAGCTAAACAT

CTGCCGGGAATAAAGCCGGTGGCGGCGCTCACGAGCGGCTGGGAGCTGCTCTCTGAGTGCCATCATCT

GTGTTCCT<u>GCTCCCACAGA</u>$_{1039}$CCCACCCTCCCAAGTGCATTCAGTGCGGGCAGTACCTGGA
                OLIGO 40

CGACCCTGACCTCAAATATGGGCAGCACCCACCAGACGCG$_{1119}$GTTCGTACAGCTCTCTTCC

CAGCCTTCCTCTGCCTGTCCCTTGTCCCACTGCTCACCAGCCCCGTGTCCTTCAGG$_{1120}$TGGATGAG

CCACAGATGCTGACAAATGAGAAGCTGTCCATCTTTGATGCCAACGAGTCTGGCTTTGAG

AGTTATGAGGCGCTTCCCCAGCACAAACTGACCTGCTTCAG$_{1229}$GTAAGTGCACTTTCGTCT
                                          SEQ ID NO 15 ←┐  ┌→ SEQ ID NO 16

GCATGTTTGCTTCGTGGAAGGAGGCACATCCCCAGAGCnnnnCCATCCTAATACGACTCACTATAG

GGCTCGAGCGGCCGCCGGGAGGTCTCTCTGTCTTCACTAAAGAACGTGCTCCCGAATGTC

AAGGGGCATCTGGACAGTGGCCGCAGTGTTTGAGATTTATGCCCAAAAGGAGGCAGAAGT

FIG. 1F

CCTTCCTTCCCACATCCCTTTTCACACTGTTCTATAACCTGCTTTATTTTCTAAATTGAGG
TCTAACTCGTATAATATAAAATTAACCATATGAGGTATCTTGAATAGGTGAATTCATAGGT
ATAGAAAGCAGATTGGTGGTTGCCGGGGGTGGGGGCTGAGGGCCGGTTGGGAGGAGACT
GGAGAGTGACTGCTACTTGATGGGAATGAGGCTTTATTAACATTTGAGTGACAGAAATGT
TCTGCAGCTGAATAGAGCTAGTGGCTGCACTGCATAGTAGAAGGTGTTCTAGAAACCGGT
ATTTCCCGCACTGTAAGTCTGACTGATCTTTTGGTGTTGCTGTTGCAGACACACATACACT
TGATGCTTAGGTGGGAGAATAAGGTAGAAACTCTGGGTGATAGAACGCTGTCTTAATCCA
GTGTTCCCGCAACCAAAAAATGAGTGTCGGGGCCAGGCATGGTGGTTCAGCCTGTAATCC
CAGCACTTTGGGAGGCTGAGGTGGGTAGATCACTGGAGATAAAGAGTTTGAGACCAGCCT
GCTACACATAGTGAAACCCCGTCCCTACTAAAAATACAACAATTAGCCGGGCATGGTGGT
TCAGGCCTGTAATCCCAGCTACTCGGGAGGCTGAGGCAGGAGAATTACTTGAACCCGGG
AGGTGGAGGCTGCAGTGAGCCAAGATTATGCCATCGCGCTCCAGCCTGAGGGATAGAGC
AAGACTCTGTCTCAAAAACAAACAAAAAAGAGTGTCAGACTTGTACATTCTCTCATTTC
CTCGTGCCTGATATGAAGTCTGCACGAAGACCCCTTCACGGCTTAGCTGGTAAGCATGTG
CTTTGT<u>TTCCTGTCTAGT</u>₁₂₃₀GTGTACTGTAAGCACGGTCACCTGTGTCCCATCGACACC
            OLIGO 41
GGCCTCATCGAGAAGAATATCGAACTCTTCTTTTCTGGTTCAGCAAAACCAATCTATGAT
GATGACCCGTCTCTTGAAG₁₃₄₈GTAAGGAATAGTCCGGGATTATGTTTGGGGGACACTTTAAAAAC
AGCCAGGCAGGTTGGCTCACATCTGTAATCCTAGCACTTTGGGGGCTGAGGCCAGAGGATCACTTGAGC
SEQ ID NO 16 ←┐       ┌→SEQ ID NO 17
CCGGGAGTTTnn~450bp~nnTTTAGTCCATTTCCTTTTTCTGCTCTAGG₁₃₄₉TGGTGTTAATGGCA
AAAATCTTGGCCCCATAAATGAATGGTGGATCACTGGCTTTGATGGAGGTGAAAAGGCCC
TCATCGG<u>CTTCAGCACCT</u>₁₄₄₁GTAAGTGTGTGGCCCATCATAGGCTGGCCGGGGTCTGAAAGGGG
           OLIGO 42
CCTTCATGTTCTCCTTCCTGGGGGCTGACGGGGCTCTGGTGGGATTCTCAGCAGGCTTGCAGAAGGCC
                         SEQ ID NO 17 ←┐
ATGTGACTGGGAACCTTAGCAGGTTCAGTTGGGGTAGATCTCTTGTGTTAGTTAGTAGGnn~900bp~n
┌→SEQ ID NO 18
nCGCTCTCTGGCTGGCTCAGACTGGCTTCTTCAGAACAAGCCAGCTATGATGTGTTGTGCCCTATGTTTC
TGACATTTGGGTACGGGATGACTTTTAGACTGTTGGGTGAGTTTGGTAGACTCCTCCATGCCCTGTGGCC
ACTGTAGGCGCCATCAGATTCCAGCCCCTTTTCCACACCTCCTCTGTTCGCCCCAGC₁₄₄₂ATTTGCC
GAATACATTCTGATGGATCCCAGTCCCGAGTATGCGCCCATATTTGGGCTGATGCAGGAG
AAGATCTACATCAGCAAGATTGTGGTGGAGTTCCTGCAGAGCAATTCCGACTCGACCTAT
GAGGACCTGATCAA<u>CAAGATCGAG</u>₁₅₉₃GTAAGAGATCGAGGGTCCTCAGCATCCGGGATTCCCA
            OLIGO 43
CTGGAAACTTGCCTTCAGAACCAGCAGACACTGTTCTTCAGTTGGATTTAGGCCAGTTTGGCTTAAGCA
TGAGAGAAACCTGTTCTCTTTCAAGA1594CCACGGTTCCTCCTTCTGGCCTCAACTTGAACCG

FIG. 1G

CTTCACAGAGGACTCCCTCCTGCGACACGCGCAGTTTGTGGTGGAGCAGGTGGAGACTTA
TGACGAGGCCGGGGACAGTGATGAGCAGCCCATCTTCCTGACGCCCTGCATGCGGGACC
TGATCAAGCTGGCTGGGGTCACGCT<u>GGGACAGAG</u>₁₇₈₁GTAAGGATGCGGCTGGGACCAGAGTG
            OLIGO 44
AAGACTGGAGACCGGGGAGGGTAGAGCATGGCCCACATCCTCTGTCCCAGTCCTCTGAGATGCTGGAA
CCTCTCCCGTAGG₁₇₈₂CGAGCCCAGGCGAGGCGGCAGACCATCAGGCATTCTACCAGGGA
GAAGGACAGGGGACCCACGAAAGCCACCACCACCAAGCTGGTCTACCAGATCTTCGATA
CTTTCTTCGCAGAGCAAATTGAAAAGGATGACAGAGAAGACAAGGAGAACGCCTTTAAG
CGCCGGCGATGTGGC<u>GTCTGTGAG</u>₁₉₆₈GTAACCTCACCTGTGGGTGCTCCCGCTCCCCTAAGGTG
        OLIGO 45
GCCCAGCCTCTGGCCTGATCTGAGGACTGCTCCATCTTTCTCTGTGGCTTGAGACTCTGGCTGCTCAAA
     SEQ ID NO 18 ←⏋ ⏌→SEQ ID NO 19
TGTGACCCTGAGACAGAAATTGTTGTGGnnnnnCTGTGCCCAGCCTGTTTGCCTTTTTATGCCTTTTTAG
G₁₉₆₉TGTGTCAGCAGCCTGAGTGTGGGAAATGTAAAGCCTGCAAGGACATGGTTAAATTT
GGTGGCACTGGACGGAGCAAGCAGGCTTGCCAAGAGCGGAG₂₀₆₆GTAGGTCAGGCCGAGTC
             OLIGO 46
TTCCTCCTGTGGCAGAGGACTTGCCAGCTGGTGGCAGATGCACTGTGGAGAAGGGCCGTCATGTGTGGG
   SEQ ID NO 19 ←⏋ ⏌→SEQ ID NO 20
ACAGCACCAGGATTCCTTCGnn~180bp~nnAGACCTGTCCCTGTTATGAAGAAAACAGCCCCGGTTG
         SEQ ID NO 20 ←⏋⏌→SEQ ID NO 21
GTCTTACTTAGAAAAGGGGCCTTAGGTATAACCAGTGACATTGCAGG₂₀₆₇TGTCCCAATATGGCCA
TGAAGGAGGCAGATGACGATGAGGAAGTCGATGATAACATCCCAGAGATGCCGTCACCC
AAAAAAATGCACCAGGGGAAGAAGAAGAAACAGAACAAGAATCGCATCTCTTGGGTCGG
            SEQ ID NO 21 ←⏋ ⏌→
AGAAGCCGTCAAG₂₂₁₄<u>GTAACCCTTGG</u>AGTCCCCTTGGTTCAGTCCTCACTGCnn~1500bp~nnA
SEQ ID NO 22 OLIGO 47         SEQ ID NO 22 ←⏋→
AGTCAAGGCCAGCAAAGACCCTCAGAATGATCCTCCATGAACTTATGCTCTCATTTTCAGA₂₂₁₅CTGA
SEQ ID NO 23
TGGGAAGAAGAGTTACTATAAGAAGGTGTGCATTGATGCGGAAACCCTGGAAGTGGGGGA
CTGTGTCTCTGTTATTCCAGATGATTCCTCAAAACCGCTGTATC<u>TAGCAAG</u>₂₃₃₀GTTTGCAT
            SEQ ID NO 23 ←⏋ OLIGO 48 ⏌→
CTTTCTTTTTGCTTGACTTCTGCATGCACTTTCTCATCAAGTAGGAGATGCCCTGTnn~150bp~nnCTC
SEQ ID NO 24
CCCATGCCCGTCTTCTATTCCAGG₂₃₃₁GTCACGGCGCTGTGGGAGGACAGCAGCAACGGGCA
GATGTTTCACGCCCACTGGTTCTGCGCAGGGACAGACACAGTCCTCGGGGCCACGTCGGA
CCCTCTGGAGCTGTTCTTGGTGGATGAATGTGAGGACATGCAGCTTTCATATATCCACAG
CAAAGTGAAAGTCATCTACAAAGCCCCCTCCGAAAACTGGGCCATGGAG₂₅₃₅GTGAGTGC
  SEQ ID NO 24 ←⏋  ⏌→SEQ ID NO 25
CTGGTGTCCTCGTGAGCCCn400bpnnnGACCCAACCGACGATATCTTTGAGT<u>CTCCCAAGG</u>₂₅₃₆GA
                OLIGO 49
<u>GGCATGGATCCCGAGTCCCTGCTGGAGGGGGACGACGGGAAGACCTACTTCTACCAGCT</u>
GTGGTATGATCAAGACTACGCGAGATTCGAGTCCCCTCCAAAAACCCAGCCAACAGAGG
ACAA<u>CAAGTTCAA</u>₂₆₆₉GTGAGCACTGGGGCTGGACTCGGGGTCAGCAGGCACTTTCAGCCCACATC
SEQ ID NO 25 LIGO 50   ←⏋  ⏌→SEQ ID NO 26
ACTCCCTTTTCCCGTGTGCTTCCGnn~850bP~nnAAGCTGGCAGTAGCTGCTGCGGCCACTGCCGGCC

FIG. 1H

ACCTCAGGGCCTTATGTTTCTGTCCCTTT<u>GTTTCCTTCAGA</u>$_{2670}$TTCTGTGTGAGCTCTGCCCGTC
                                      OLIGO 51
TGGCTGAGATGAGGCAAAAAGAAATCCCCAGGGTCCTGGAGCAGCTCGAGGACCTGGAT
AGCCGGGTCCTCTACTACTCAGCCACCAAGAACGGCATCCTGTACCGAGTTGGTGATGGT
                                                                               SEQ ID
GTGTACCTGCCCCCTGAGGCCTTCACGTTCAA$_{2843}$GTAAGTGCCCCCTCGGAGCAGCCGGGGC
NO 26 ←⏋         ⏌→SEQ ID NO 27
CAGGGGnn~450bP~nnAAATCATTTCTTAGGGTACACACCTACCTTAATTCATCAGGTGCTTGACTTT
AAATGGTTATTTTCACTGGTCAGTCATGCCTGACTGACCACTGCAAGGTGGAAGGTTCATTGATGTCAA
GTGGGTGC<u>TTCTCTGCAGC</u>$_{2844}$ATCAAGCTGTCCAGTCCCGTGAAACGCCCACGGAAGGAGC
          OLIGO 52
CCGTGGATGAGGACCTGTACCCAGAGCACTACCGGAAATACTCCGACTACATCAAAGGC
AGCAACCTGGATGCCCCTGAGCCCTACCGAATTGGCCGGATCAAAGAGATCTTCTGTCCC
AAGAAGAGCAACGGCAGGCCCAATGAGACTGACATCAAAATCCGGGTCAACAAGTTCTA
CAG$_{3065}$GTCAGCAGAGGCCTCTGTTCTTCCTCGAGGCCACAGACTCTTCTAGAAGGCTCTGCTGAAAC
SEQ ID NO 27 ←⏋         ⏌→SEQ ID NO 28
AAGGTTGTGGnn~520bp~nnAAAAGGAGAGCTCCTAACGAGGCCTACTCCCGCTCGCAGG$_{3066}$CCT
GAGAACACCCACAAGTCCACTCCAGCGAGCTACCACGCAGACATCAACCTGCTCTACTG
GAGCGACGAGGAGGCCGTGGTGGACTTCAAGGCTGTGCAGGGCCGCTGCACCGTGGAGT
ATGGGGAGGACCTGCCCGAGTGCGTCCAGGTGTACTCCATGGGCGGCCCCAACCGCTTC
TAC<u>TTCCTCGAG</u>$_{3258}$GTGGTGCCCCTGCTTGCTAGAGGGAAGGCTTCGGGGTCAAAGTTGGCCAGA
     OLIGO 53
AGGAGTCTGATGTCGGGTTATACACAAGGCGGCTTGGCTGCAGGGTTTCAGCTTTTGTAAGAAGTGGGT
                              SEQ ID NO 28 ←⏋        ⏌→SEQ ID NO 29
GGTTGGCTGACGTGAAGCTGTTCTGCAGGAGCTTTACGGGGGnn~950bp~nnGTCAACTACTCTATTG
GTGGCTAATTGGTCATGGCCCCACTGAGGAGAATTAAGTGACTATCAATTGCCTTCTTACTAGTCTGCGT
TAGAGAGGGGACAGTGGCGTTTCTCTCCCAAACGATTGCAGTTCTCTCCTTTTCAGG$_{3259}$CCTATAAT
GCAAAGAGCAAAAGCTTTGAAGATCCTCCCAACCATGCCCGTAGCCCTGGAAACAAAGG
GAAGGGCAAGGGAAAAG$_{3343}$GTACGTCATTGTATGAGTTTCTTTTCAAGTTATTCTTCTGTAACTTG
GAGGCTGCCTGTGAATCCCTCAGTGTAAAACCACCTCTGGTGTTACTGACTCTGGGACAGCGAGGCCGC
CTGAGTTAACAAGGCGCTTGAGAGCAAGGTGGACTTGGACTCTGAGGATCGGGTTTAGCCTCTGGCCTC
TCTCCCCCAGG$_{3344}$GAAGGGCAAGCCCAAGTCCCAAGCCTGTGAGCCGAGCGAGCCAGAG
             OLIGO 54
ATAGAGATCAAGCTGCCCAAGCTGCGGACCCTGGATGTGTTTTCTGGCTGCGGGGGGTTG
TCGGAGGGATTCCA<u>CCAAGCAG</u>$_{3472}$GTGAGCGCCCGTAGGCTCCATCTCTGAATACCTGGTGAGC
              OLIGO 55
CCAGACCGGGCAGGTGCTACCTGAAACGACTTCCAACCCGGTCACCTTCTGATCTAAGAATCTCTTCGA
SEQ ID NO 29 ←⏋        ⏌→SEQ ID NO30
GGCCAGGCACGnn~500bp~nnACTGCACGCCAGCCTGGGTGACAGAGCGAGACTCCATCTCAAAAA
AAAAAAAAAAATCTTCTGGAGAGTTGAAAGCATGGCTTCGTGCTTGATCTGCCAGG$_{3473}$CATCTCTG
ACACGCTGTGGGCCATCGAGATGTGGGACCCTGCGGCCCAGGCGTTCCGGCTGAACAAC

FIG. 1I

CCCGGCTCCACAGTGTTCACAGAGGACTGCAACATCCTGCTGAAGCTGGTCATGGCTGGG
GAGACCACCAACTCCCGCGGCCAGCGGCTGCCCCAGAAGGGAGACGTGGAGATGCTGTG
CGGCGGGCCGCCCTGCCAGGGCTTCAGCGGCATGAACCGCTTCAATTCGCGCACCTACT
CCAAGTTCAAAAACTCTCTGGTGGTTTCCTTCCTCAG$_{3755}$GTAAACGGGTAGAAGCCCCCAG
                          SEQ ID NO 30 ←        →SEQ ID NO 31
TGTTGCCAGACGGCCCGGGGCTGTGCGCATGTCAGCAGTGTCATTTnn~250bp~nnnGAAGCTGACAG
CTCAGCTCTCACCAGGGAGAGACTTTGATAACATTCGTGAGGGGCTTCCGGCACAGTGGGCGTTTCTTC
CCTCTGTCTGTGGAGCTGACTCCTGCAGTCTCTCCTGCCCCCTACAGCAGC$_{3756}$TACTGCGACTAC
TACCGGCCCCGGTTCTTCCTCCTGGAGAATGTGAGGAACTTTGTCTCCTTCAAGCGCTCC
ATGGTCCTGAAGCTCACCCTCCGCTGCCTGGTCCGCATGGGCTATCAGTGCACCTTCGGC
GTGCTGCAG$_{3897}$CTGGGCCCTGGGGCTGGGGCGGGCAGACAGATGAGGCCAGCACGTGACCCGGCC
AGCAGCCAGCCATCCCTTACTGAAGGCAGGGTTCAATGGCATAGGCCTGCCATCCAGGCAGCAGAGGC
                     SEQ ID NO 31 ←       →SEQ ID NO 32
TGGCATGGTGCTCTGTCCACTGGCGGATGAGGGGAGATCGnn~1200bp~nnCGACTCAGCTGCTGAC
CCTGGGCCTGGGTCTGGCCAGTCCAGTTGGGAGTGTCCCACTCACGGTGGGGTTGTCCGTCC<u>TTCTCCC</u>
<u>CCACAGG</u>$_{3898}$<u>CCGGTCAGTACGGCGTGGCCCAGACTAGGAGGCGGGCCATCATCCTGGCC</u>
     OLIGO 56
GCGGCCCCTGGAGACAAGCTCCCTCTGTTCCCGGAGCCACTGCACGTGTTTGCTCCCCGG
GCCTGCCAGCTGAGCGTGGTGGTGGATGACAAGAAGTTTCTGAGCAACATAACCAG4064GTAGG
                    SEQ ID NO 35 ← OLIGO 57 →SEQ ID
TGGCCCCCGTCGCTCCTCCACACACTGCCGACGAGGCCTCAGTAGCTCATGGGGnn~600bP~nnCATAGC
NO 36
CCCATCCCCCCTTCCAGATGGCATCCAGCACACTGCCACCCATGTGACCTCGGGCAGTGCTGTGATCT
CGGGAGAAGGCCATCTGAGCAGGCAGGGGGTGGCACCTGTGATGAGGGGACAGCTGCTGCGTGCATCT
CCAGAGGTGTTGACCTCCTCCTCTGTTGCAGG4O65TTGAGCTCGGGTCCTTTCCGGACCATCACGGTGC
GAGACACGATGTCCGACCTGCCGGAGGTGCGGAATGGAGCCTCGGCACTGGAGATCTCCTACAACGGG
GAGCCTCAGTCCTGGTTCCAGAGGCAGCTCCGGGGCGCACAGTACCAGCCCATCCTCAGGGACCACAT
<u>CTGTAAG4242GTAATGGCACCC</u>TGACAGAGCGGCTCCTCCTCGAGGCCCAGCCCAGCAGCCTCGTGGG
   OLIGO 58
AACAGTCAGCCTGCCCAAGACTCAGGGGAGACATGGAATCTGATCCCAGGCTCCTCCTCCGAGTCTCA
SEQ ID NO 33 ←     →SEQ ID NO 34
GCCTTTGTGTGAnn~600bp~nnnATGGACACGTCCCCCCACACTCTTTCAGG4243A4244CATGAGTGCATT
GGTGGCTGCCCGCATGCGGCACATCCCCTTGGCCCCAGGGTCAGACTGGCGCGATCTGCCCAACATCG
AGGTGCGGCTCTCAGACGGCACCATGGCCAGGAAGCTGCGGTATACCCACCATGACAGGAAGAACGGC
CGCAGCAGCTCTGGGGCCCTCCGTGGGGTCTGCTCCT<u>GCGTGGAAG</u>4438GTGGGTCCTGTAACTTCTGG
                         SEQ ID NO 34 ← OLIGO 59 →SEQ ID NO 35
TTCCCGGTGGCTGAGGGGAAGGAAGGCAGACCTGGGCCTTTnn~800bp~nnGACAGAGTCCCATCTCTGC
CTCCCAAAGCTCTAACAGCCATGTCCCAAGCCTATACCCCATCCCACAACTGCAGCCTCATCACTGTC
CTGTCTTCCAGC4439CGGCAAAGCTGCGACCCCGCAGCCAGGCAGTTCAACACCCTCATCCCCCTGGT

GCCTGCCCCACACCGGGAACCGGCACAACCACTGGGCTGGCCTCTATGGAAGGCTCGAGTGGGACGGC

TTCTTCAGCACAACCGTCACCAACCCCGAGCCCATGGGCAAGCAG4605GTAGGTGGGGAGGGGGGATC

CGAGGGCCTGGGTCAGGCTGTACTTGGCGGCCTAACTAGGTGGAAGTGTGGGTTTAGCCAAGTGGGGGA

SEQ ID NO 35 ←┐          ┌→SEQ ID NO 36
CAGCACCCCAGGATCCCCCAGGCACCTGnn~400bp~nnAGACTGCTCTGCCTCCTGCCCCTCCACGTCCA

CGGACAAGCTCATAGCCAAGCCATGGCCGTATGCTGTCACAGTGCCATTTCCCTCCCTGTCCCCGACG

GTGACCCGGCCTGGGTGCTACTGCCCTCGCCCACCGCGCCTCTTTCCCCCAGG$_{4606}$GCCGCTGCTCC
                                                          OLIGO 60
ACCCAGAGCAGCACCGTGTGGTGAGCGTGCGGGAGTGTGCCCGCTCCCAGGGCTTCCCTGACACCTAC

CGGCTCTTCGGCAACATCCTGGACAAGCACCGGCAG$_{4722}$GTCAGTGGGGCGGCGCGCTGGGTCTGGAC
                                           OLIGO 61    SEQ ID NO 36 ←┐      ┌→
AGGAAGGAGGCTTCTGTGCCTGTCACCAGGTGGGGCTGGGGCAGCGCAGTCACTTnn~1450bp~nnCAATG
SEQ ID NO 37
CCCAGGGTTGTCCTCCATCTGAGCAGGTGCTGGAGTACACCTCCCCCGGCCTTGGGCCTGGTGTCCACAT

CAGGCATTGCCCTTCTCCCCTCCTGCAGG4723TGGGCAATGCCGTGCCACCGCCCCTGGCCAAAGCCA

TTGGCTTGGAGATCAAGCTTTGTATGTTGGCCAAAGCCCGAGAGAGTGCC$_{4809}$GTATGGTGGGGTGGGC
                                    SEQ ID NO 37 ←┐  OLIGO 62 ┌→SEQ ID NO 38
CAGGCTTCCTCTGGGGCCTGACTGCCCTCTGGGGTACATGTGGGGGCAGhnn~550bp~nnACTGAGCCTCTG

GGTCTAGAACCTCTGGGGACCGTTTGAGGAGTGTTCAGTCTCCGTGAACGTTCCCTTAGCACTCTGCCA

CTTATTGGGTCAGCTGTTAACATCAGTACGTTAATGTTTCCTGATGGTCCATGTCTGTTACTCGCCTGTC

AAGAGGCGTGACACCGGGCGTGTTCCCCAGAGTGACTTTTCCTTTTATTTCCCTT4810CAGCTAAAATA

AAGGAGGAGGAAGCTGCTAAGGACTAGTTCTGCCCTCCCGTCACCCCTGTTTCTGGCACCAGGAATCC

CCAACATGCACTGATGTTGTGTTTTAACATGTCAATCTGTCCGTTCACATGTGTGGTACATGGTGTTTG

TGGCCTTGGCTGACATGAAGCTGTTGTGTGAGGTTCGCTTATCAACTAATGATTTAGTGATCAAATTGTG

CAGTACTTTGTGCATTCTGGATTTTAAAAGTTTTTTATTATGCATTATATCAAATCTACCACTGTATAGT
                                                              SEQ ID NO 38 ←┐
GGAAATTAAGACTTTATGTAGTTTTTATATGTTGTAATATTTCTTCAAATAAATCTCTCCTATAAACCA5169

FIG. 1J

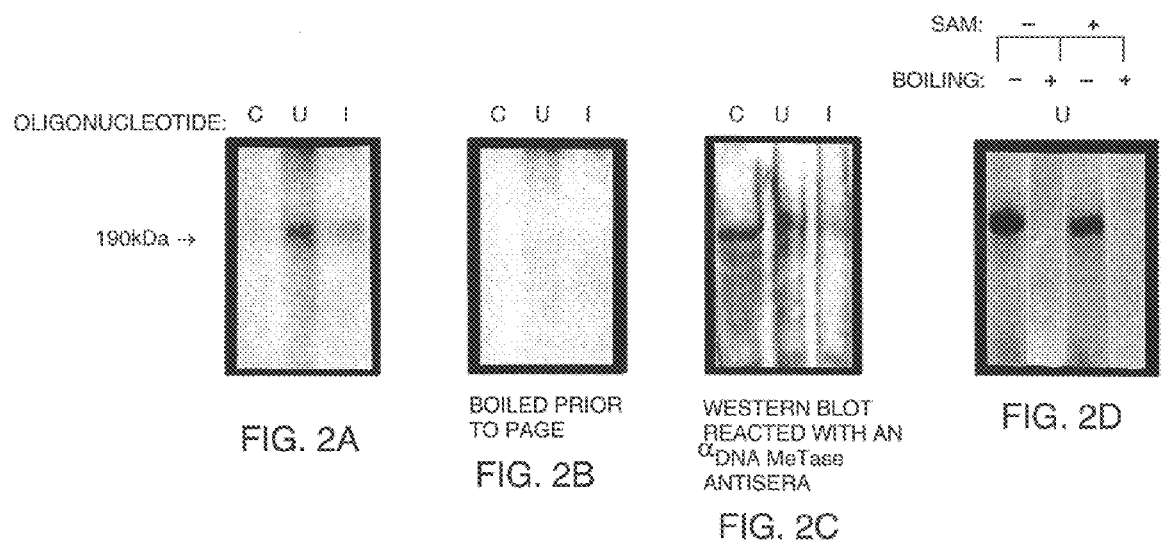

DNA METHYLTRANSFERASE GENOMIC SEQUENCES AND ANTISENSE OLIGONUCLEOTIDES

This is a continuation-in-part of Ser. No. 08/866,340, filed May 30, 1997, now U.S. Pat. No. 6,020,318. This application claims priority to U.S. Ser. No. 60/069,865, filed Dec. 17, 1997.

BACKGROUND OF THE INVENTION

1. Field of the Invention

The invention relates to modulation of gene expression. In particular, the invention relates to modulation of gene expression of the gene encoding DNA methyltransferase, and to modulation of gene expression that is regulated by the enzyme DNA methyltransferase.

2. Summary of the Related Art

Modulation of gene expression has become an increasingly important approach to understanding various cellular processes and their underlying biochemical pathways. Such understanding enriches scientific knowledge and helps lead to new discoveries of how aberrancies in such pathways can lead to serious disease states. Ultimately, such discoveries can lead to the development of effective therapeutic treatments for these diseases.

One type of cellular process that is of particular interest is how the cell regulates the expression of its genes. Aberrant gene expression appears to be responsible for a wide variety of inherited genetic disorders, and has also been implicated in numerous cancers and other diseases. Regulation of gene expression is a complex process, and many aspects of this process remain to be understood. One of the mysteries of this process resides in the fact that while the genetic information is the same in all tissues that constitute a multicellular organism, the expression of functions encoded by the genome varies significantly in different tissues.

In some cases, tissue-specific transcription factors are known to play a role in this phenomenon. (See Maniatis et al., Science 236: 1237–1245 (1987); Ingarham et al., Annual Review of Physiology 52: 773–791 (1990). However, several important cases exist that cannot be readily explained by the action of transcription factors alone. For example, Midgeon, Trends Genet. 10: 230–235 (1994), teaches that X-inactivation involves the inactivation of an allele of a gene that resides on the inactive X-chromosome, while the allele on the active X-chromosome continues to be expressed. In addition, Peterson and Sapienza, Annu. Rev. Genet. 27: 7–31 (1993), describes "parental imprinting", where an allele of a gene that is inherited from one parent is active and the other allele inherited from the other parent is inactive. In both of these cases, both alleles exist in an environment containing the same transcription factors, yet one allele is expressed and the other is silent. Thus, something other than transcription factors must be involved in these phenomena.

Investigators have been probing what type of "epigenetic information" may be involved in this additional control of the expression pattern of the genome. Holliday, Philos. Trans. R. Soc. Lond. B. Biol. Sci. 326: 329–338 (1990) discusses the possible role for DNA methylation in such epigenetic inheritance. DNA contains a set of modifications that is not encoded in the genetic sequence, but is added covalently to DNA using a different enzymatic machinery. These modifications take the form of methylation at the 5 position of cytosine bases in CpG dinucleotides. Numerous studies have suggested that such methylation may well be involved in regulating gene expression, but its precise role has remained elusive. For example, Lock et al., Cell 48: 39–46 (1987), raises questions about whether the timing of hypermethylation and X-inactivation is consistent with a causal role for methylation. Similarly, Bartolomei et al., Genes Dev. 7: 1663–1673 (1993) and Brandeis et al., EMBO J. 12: 3669–3677 (1993), disclose timing/causation questions for the role of methylation in parental imprinting.

Some of the shortcomings of existing studies of the role of DNA methylation in gene expression reside in the tools that are currently available for conducting the studies. Many studies have employed 5-azaC to inhibit DNA methylation. However, 5-azaC is a nucleoside analog that has multiple effects on cellular mechanisms other than DNA methylation, thus making it difficult to interpret data obtained from these studies. Similarly, 5-azadC forms a mechanism based inhibitor upon integration into DNA, but it can cause trapping of DNA methyltransferase (hereinafter, DNA MeTase) molecules on the DNA, resulting in toxicities that may obscure data interpretation.

More recently, Szyf et al., J. Biol. Chem. 267: 12831–12836 (1995), discloses a more promising approach using expression of antisense RNA complementary to the DNA MeTase gene to study the effect of methylation on cancer cells. Szyf and von Hofe, U.S. Pat. No. 5,578,716, discloses the use of antisense oligonucleotides complementary to the DNA MeTase gene to inhibit tumorigenicity. These developments have provided powerful new tools for probing the role of methylation in numerous cellular processes. In addition, they have provided promising new approaches for developing therapeutic compounds that can modulate DNA methylation. One limitation to these approaches is that their effect is not immediate, due to the half life of DNA MeTase enzyme. Thus, although the expression of DNA MeTase is modulated, residual DNA MeTase enzyme can continue to methylate DNA until such residual enzyme is degraded. Polysome-associated DNA MeTase mRNA may also persist for some time, allowing additional translation to produce additional DNA MeTase enzyme. There is, therefore, a need for new antisense oligonucleotides which can act against intron regions of DNA MeTase RNA in the nucleus before its processing and association with polysomes. The development of such oligonucleotides will require obtaining sequence information about the non-coding regions of DNA MeTase RNA.

BRIEF SUMMARY OF THE INVENTION

The invention provides recombinant nucleic acids comprising nucleic acid sequences from the genomic DNA methyltransferase gene (DNA MeTase). The invention also provides recombinant nucleic acids comprising nucleic acid sequences complementary to the genomic DNA MeTase gene. The invention further provides sequence information for such nucleic acid sequences. In addition, the invention provides antisense oligonucleotides complementary to special target regions of the genomic DNA MeTase gene or its RNA transcript. Finally, the invention provides methods for using such antisense oligonucleotides as analytical and diagnostic tools, as potentiators of transgenic plant and animal studies and for gene therapy approaches, and as potential therapeutic agents.

In a first aspect, the invention provides novel recombinant nucleic acid sequences comprising at least one nucleotide sequence selected from the nucleotide sequences of the genomic DNA MeTase gene. The sequence of the sense strand of the genomic DNA MeTase gene is shown in FIG.

1. The nucleotide sequence of the sense strand of the DNA MeTase gene is also set forth in the Sequence Listings as SEQ ID NO 1, SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 22, SEQ ID NO 23, SEQ ID NO 24, SEQ ID NO 25, SEQ ID NO 26, SEQ ID NO 27, SEQ ID NO 28, SEQ ID NO 29, SEQ ID NO 30, SEQ ID NO 31, SEQ ID NO 32, SEQ ID NO 33, SEQ ID NO 34, SEQ ID NO 35, SEQ ID NO 36, SEQ ID NO 37, and SEQ ID NO 38.

In a second aspect, the invention provides novel recombinant nucleic acid sequences complementary to at least one nucleotide sequence selected from the nucleotide sequences set forth in the Sequence Listings as SEQ ID NO 1, SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 22, SEQ ID NO 23, SEQ ID NO 24, SEQ ID NO 25, SEQ ID NO 26, SEQ ID NO 27, SEQ ID NO 28, SEQ ID NO 29, SEQ ID NO 30, SEQ ID NO 31, SEQ ID NO 32, SEQ ID NO 33, SEQ ID NO 34, SEQ ID NO 35, SEQ ID NO 36, SEQ ID NO 37, and SEQ ID NO 38.

In a third aspect, the invention provides antisense oligonucleotides which inhibit the expression of DNA MeTase. Such antisense oligonucleotides are complementary to a special target region of RNA or double-stranded DNA that encodes DNA MeTase. Preferably, such antisense oligonucleotides contain one or more modified internucleoside linkage and may optionally contain either deoxyribonucleosides, ribonucleosides or 2'-O-substituted ribonucleosides, or any combination thereof. Particularly preferred antisense oligonucleotides according to this aspect of the invention include chimeric oligonucleotides and hybrid oligonucleotides.

In a fourth aspect, the invention provides a method for investigating the role of DNA MeTase in cellular growth, including the growth of tumor cells. In the method according to this aspect of the invention, the cell type of interest is contacted with an antisense oligonucleotide according to the invention, resulting in inhibition of expression of DNA MeTase in the cell. The antisense oligonucleotides can be administered at different points in the cell cycle, or in conjunction with promoters or inhibitors of cell growth to determine the role of DNA MeTase in the growth of the cell type of interest.

In a fifth aspect, the invention provides methods for inhibiting tumor growth comprising administering to a mammal, including a human, antisense oligonucleotides according to the invention. In the method according to this aspect of the invention a therapeutically effective amount of an antisense oligonucleotide according to the invention is administered for a therapeutically effective period of time to a mammal, including a human, which has tumor cells present in its body.

BRIEF DESCRIPTION OF THE DRAWINGS

FIGS. 1A–J shows the nucleotide sequence for the sense strand of the DNA MeTase gene comprising the nucleotide acid sequences set forth in the Sequence Listings as SEQ ID NO 1, SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 22, SEQ ID NO 23, SEQ ID NO 24, SEQ ID NO 25, SEQ ID NO 26, SEQ ID NO 27, SEQ ID NO 28, SEQ ID NO 29, SEQ ID NO 30, SEQ ID NO 31, SEQ ID NO 32, SEQ ID NO 33, SEQ ID NO 34, SEQ ID NO 35, SEQ ID NO 36, SEQ ID NO 37, and SEQ ID NO 38. Nucleotides in coding regions are identified as bold characters. Subscript numbers correspond to the DNA MeTase cDNA numbering of Yen et al. (Nucleic Acids Res. 20(9): 2287–2291 (1992) and Yoder et al. (J. Biol. Chem. 271: 31092–31097 (1996)). Preferred special target regions are underlined.

FIGS. 2A–D are representations of autoradiographs (panels A, B and D) and Western blots (panel C) in an experiment to identify complex formation between the oligonucleotides of the invention and DNA MeTase enzyme. Complex formation was reversed by boiling, and was independent of SAM.

FIG. 4 Panel (B) is a schematic representation showing the exon-intron structure of the human DNA MeTase gene. Sub-clones shown in panel (A) were exon sequenced to determine exon-intron boundaries. Exons are depicted as vertical bars and numbered above, introns as thick horizontal bars. Regions containing exons coding for specific function domains are depicted, NLS=nuclear localisation signal, FTR=replication foci targeting region, Zn=zinc binding domain, AdoMet Binding=S-adenosyl-methionine binding motif, Pro-Cys =proline-cysteine catalytic motif, Catalytic Domain=region conserved in all CpG methyltransferases. Exonal location of proposed initiation codons=ATG.

FIG. 4 Panel (C) shows the positions of exons determined by PCR analysis and verified by Southern blot analysis. The fragments encoding the different segments of the human DNA MeTase mRNA were visualized by hybridization to the following cDNA probes: 1. A probe bearing the first exon. 2. A probe bearing exons 3–5 (starting spanning nucleotides 415–740 of the known cDNA) 3. A probe bearing exons 7–20 4. A probe spanning exons 30–40. The cDNA probes are indicated under the map of the exon-intron structure, the dashed lines delineate the boundaries of exons spanned by each of the probes. The fragments visualized by each of the restriction enzymes are indicated by different shaded arrows. The size of the visualized fragments is indicated next to the arrows. The size of the fragments visualized by each of the probes corresponds to the size predicted by the restriction enzyme analysis of the genomic phages.

DETAILED DESCRIPTION OF THE PREFERRED EMBODIMENTS

Figure 3:
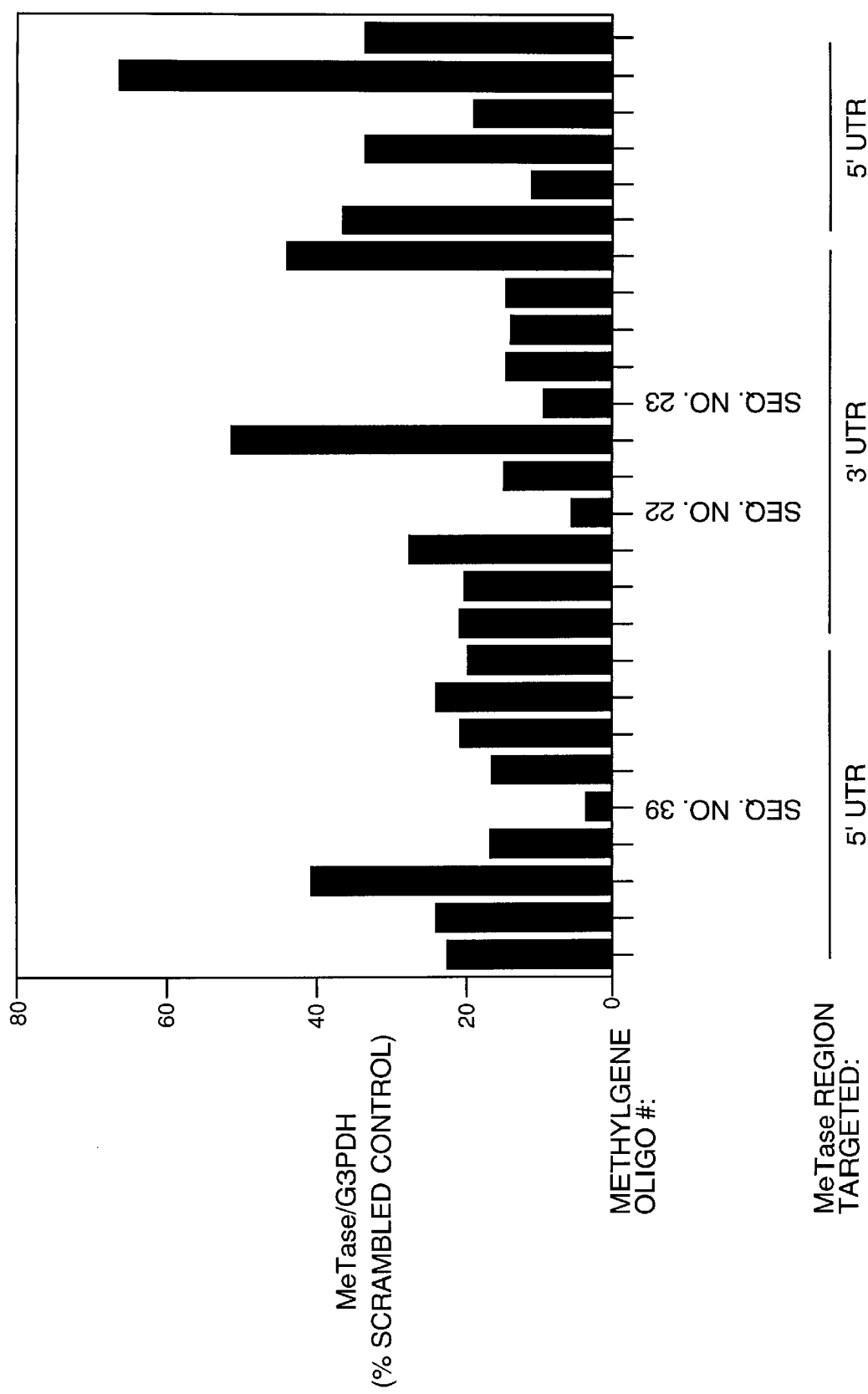
FIG. 3 is a graphic representation showing the ability of representative, nonlimiting, synthetic oligonucleotides of the invention to inhibit DNA MeTase activity in the nuclear extracts.

The invention relates to modulation of gene expression. In particular, the invention relates to modulation of gene expression of the gene encoding DNA methyltransferase (DNA MeTase), and to modulation of gene expression that is regulated by the enzyme DNA MeTase. The patents and publications identified in this specification are within the knowledge of those skilled in this field and are hereby incorporated by reference in their entirety.

The invention provides recombinant nucleic acids comprising nucleic acid sequences from the genomic DNA MeTase gene. The invention further provides sequence information for such nucleic acid sequences. In addition, the invention provides antisense oligonucleotides complementary to regions of the genomic DNA MeTase gene or its RNA transcript which could not be targeted in the absence of such information. Finally, the invention provides methods for using such antisense oligonucleotides as analytical and diagnostic tools, as potentiators of transgenic plant and animal studies and gene therapy approaches, and as potential therapeutic agents.

In a first aspect, the invention provides novel recombinant nucleic acid sequences comprising at least one nucleotide sequence selected from the nucleotide sequences of the genomic DNA MeTase gene. The sequence of the sense strand of the genomic DNA MeTase is shown in FIG. 1. Coding regions are identified as bold sequences.

In one preferred embodiment, the recombinant DNA molecule according to the invention comprises at least one nucleotide sequences selected from the nucleotide sequences shown in FIG. 1 and corresponding to Sequence Listings SEQ ID NO 1, SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 22, SEQ ID NO 23, SEQ ID NO 24, SEQ ID NO 25, SEQ ID NO 26, SEQ ID NO 27, SEQ ID NO 28, SEQ ID NO 29, SEQ ID NO 30, SEQ ID NO 31, SEQ ID NO 32, SEQ ID NO 33, SEQ ID NO 34, SEQ ID NO 35, SEQ ID NO 36, SEQ ID NO 37, and SEQ ID NO. 38 in a replicatable vector. As used herein, the term "replicatable vector" designates a nucleic acid vector able to replicate in at least one cell type. Many such replicatable vectors are well known in the art (see e.g., *Molecular Cloning*, 2d Edition, Cold Spring Harbor Laboratory Press (1989)).

In an additional preferred embodiment, the recombinant DNA molecule according to the invention comprises nucleotide sequences complementary to at least a portion of the nucleotide sequence shown in FIG. 1, and corresponding to at least one of the nucleotide sequences set forth as Sequence Listings SEQ ID NO 1, SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 22, SEQ ID NO 23, SEQ ID NO 24, SEQ ID NO 25, SEQ ID NO 26, SEQ ID NO 27, SEQ ID NO 28, SEQ ID NO 29, SEQ ID NO 30, SEQ ID NO 31, SEQ ID NO 32, SEQ ID NO 33, SEQ ID NO 34, SEQ ID NO 35, SEQ ID NO 36, SEQ ID NO 37, and SEQ ID NO 38 in a replicatable vector.

In another preferred embodiment, the replicatable vector is an expression vector. The term "expression vector" refers, in one embodiment, to a replicatable vector able to support the translation of part or all of its sequences into one or more peptides. The expression vector of this invention may replicate autonomously in the host cell, or may become integrated into the host cell DNA. The expression vector can be used to transform a host cell which is capable of expressing the nucleotide sequence shown in FIG. 1.

In yet another preferred embodiment, the term expression vector refers to a vector capable of supporting the transcription of part or all of its sequences into one or more transcripts. The vector according to this embodiment of the invention may replicate autonomously in the host cell, or may become integrated into the host cell DNA. The vector can be used to transform a host cell which is capable of transcription of the nucleotide sequence complementary to the nucleotide sequence shown in FIG. 1. Preparation of recombinant DNA molecules and expression vectors and their use to transform host cells is well known in the art (see e.g., *Molecular Cloning*, 2d Edition, Cold Spring Harbor Laboratory Press (1989)).

In yet another embodiment, the invention also provides a host cell comprising recombinant DNA molecules according to the invention. According to this invention the term "host cell" refers to a cell which expresses the nucleotide sequences according to this invention.

This first aspect of the invention further provides a method for preparing DNA MeTase enzyme or a fragment thereof. The method according to this aspect of the invention comprises culturing a host cell in an appropriate culture media to express the nucleotide sequences according to the invention. Consequently, the host cell of the invention produces DNA MeTase enzyme or a fragment thereof, which may be conveniently separated from the host cell and the culture media by affinity binding, as described in detail in this specification. Fragments of DNA MeTase enzyme can then be used to produce antibodies specific for epitopes of DNA MeTase enzyme, according to standard immunological procedures. Such antibodies can be used to purify DNA MeTase enzyme, or to quantify it in conventional immunological assays.

In a second aspect, the invention provides a novel recombinant nucleic acid molecule comprising nucleic acid sequences complementary to at least part of the genomic DNA MeTase gene. The sequence of the sense strand of the genomic DNA MeTase is shown in FIG. 1. Coding regions are identified as bold sequences. For purposes of the invention, "complementary" means being sufficiently complementary to have the ability to hybridize to a genomic region, a gene, or an RNA transcript thereof under physiological conditions. Such hybridization is ordinarily the result of base-specific hydrogen bonding between complementary strands, preferably to form Watson-Crick or Hoogsteen base pairs, although other modes of hydrogen bonding, as well as base stacking can also lead to hybridization. As a practical matter, such complementarity can be inferred from the observation of specific DNA MeTase gene expression inhibition.

In one preferred embodiment, the recombinant DNA molecule according to the invention comprises nucleotide acid having a sequence complementary to at least part of the nucleotide sequences shown in FIG. 1, and complementary to at least one of the nucleotide sequences set forth in the Sequence Listings as SEQ ID NO 1, SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 22, SEQ ID NO 23, SEQ ID NO 24, SEQ ID NO 25, SEQ ID NO 26, SEQ ID NO 27, SEQ ID NO 28, SEQ ID NO 29, SEQ ID NO 30, SEQ ID NO 31, SEQ ID NO 32, SEQ ID NO 33, SEQ ID NO 34, SEQ ID NO 35, SEQ ID NO 36, SEQ ID NO 37, and SEQ ID NO 38 in a replicatable vector. In another preferred embodiment the replicatable vector is an expression vector. The replicatable vectors and expression vectors appropriate for this aspect of the invention are generally the same well known materials as discussed for the first aspect of the invention.

In yet another embodiment, the invention provides a host cell comprising recombinant DNA molecules according to the invention. This second aspect of the invention further provides a method for inhibiting DNA MeTase enzyme expression in a transfected cell or transgenic animal. The method according to this aspect of the invention comprises culturing a host cell in an appropriate culture media to express the nucleotide sequences according to this aspect of the invention. Consequently, the host cell of the invention produces decreased levels of DNA MeTase enzyme.

In a third aspect, the invention provides antisense oligonucleotides which inhibit the expression of DNA MeTase. Such antisense oligonucleotides are complementary to a special target region of RNA or double-stranded DNA that encodes DNA MeTase.

The term "special target region" is used to denote sequences which could not be targeted without the sequence information provided by the invention. In particular, such special target regions comprise a portion of the non-coding region of the nucleic acid shown in FIG. 1. Most preferably, such special target region comprises from about 2 to about 50 nucleotides of such noncoding sequences. Such special target regions include, without limitation, intronic sequences, untranslated 5' and 3' regions as well as intron-exon boundaries from the DNA methyltransferase gene. In certain embodiments, said target region may further comprise coding regions from the DNA MeTase gene.

Preferred non-limiting examples of antisense oligonucleotides complementary to special target regions of RNA or double-stranded DNA encoding DNA MeTase according to the invention are shown in Table 1. Additional preferred oligonucleotides complementary to such special target regions have nucleotide sequences of from about 21 to about 35 nucleotides which include the nucleotide sequences shown in Table 1. Yet additional preferred oligonucleotides complementary to such special target regions have nucleotide sequences of from about 13 to about 19 nucleotides of the nucleotide sequences shown in Table 1.

TABLE 1

| SEQ. ID NO. | SEQUENCE | TARGET (*) |
|---|---|---|
| 39 | 5' AGA ACT GAC TTA CCT CGG AT 3' | 222 |
| 40 | 5' AGG GTG GGT CTG TGG GAG CA 3' | 1039 |
| 41 | 5' CAG TAC ACA CTA GAC AGG AA 3' | 1230 |

TABLE 1-continued

| SEQ. ID NO. | SEQUENCE | TARGET (*) |
|---|---|---|
| 42 | 5' CAC ACT TAC AGG TGC TGA AG 3' | 1441 |
| 43 | 5' GAT CTC TTA CCT CGA TCT TG 3' | 1593 |
| 44 | 5' CGC ATC CTT ACC TCT GTC CC 3' | 1782 |
| 45 | 5' GGT GAG GTT ACC TCA CAG AC 3' | 1968 |
| 46 | 5' GGC CTG ACC TAC CTC CGC TC 3' | 2066 |
| 47 | 5' CCA AGG GTT ACC TTG ACG GC 3' | 2214 |
| 48 | 5' AAA GAT GCA AAC CTT GCT AG 3' | 2330 |
| 49 | 5' TCC ATG CCT CCC TTG GGT AG 3' | 2536 |
| 50 | 5' CCA GTG CTC ACT TGA ACT TG 3' | 2669 |
| 51 | 5' ACA CAG AAT CTG AAG GAA AC 3' | 2670 |
| 52 | 5' AGC TTG ATG CTG CAG AGA AG 3' | 2844 |
| 53 | 5' CAG GGG CAC CAC CTC GAG GA 3' | 3258 |
| 54 | 5' CTT GCC CTT CCC TGG GGG AG 3' | 3344 |
| 55 | 5' ACG GCC GCT CAC CTG CTT GG 3' | 3473 |
| 56 | 5' TCC CGG CCT GTG GGG GAG AA 3' | 3898 |
| 57 | 5' GGG CCA CCT ACC TGG TTA TG 3' | 4064 |
| 58 | 5' GGG TGC CAT TAC CTT ACA GA 3' | 4242 |
| 59 | 5' ACA GGA CCC ACC TTC CAC GC 3' | 4438 |
| 60 | 5' GCA CGC GGC CCT GGG GGA AA 3' | 4606 |
| 61 | 5' GCC CCA CTG ACT GCC GGT GC 3' | 4722 |
| 62 | 5' CCC GGG TGG TAT GCC GTG AG 3' | 4809 |
| 63 | 5' CTG CTC TTA CGC TTA GCC TC 3' | 442 |
| 64 | 5' GAA GGT TCA GCT GTT TAA AG 3' | 443 |
| 65 | 5' GTT TGG CAG GGC TGT CAC AC 3' | 519 |
| 66 | 5' CTG GCC CTA CCT GGT CTT TG 3' | 597 |
| 67 | 5' CTA GCA ACT CTG TCA AGC AA 3' | 633 |
| 68 | 5' TAG AGC TTT ACT TTT TCA TC 3' | 717 |
| 69 | 5' GTT TGG GTG TTC TGT CAC AG 3' | 753 |
| 70 | 5' GTT TGG CAG CTC TGC AGG GT 3' | 876 |

For purposes of the invention, the term "oligonucleotide" includes polymers of two or more deoxyribonucleosides, ribonucleosides, or 2'-O-substituted ribonucleoside residues, or any combination thereof. Preferably, such oligonucleotides have from about 8 to about 50 nucleoside residues, and most preferably from about 12 to about 30 nucleoside residues. The nucleoside residues may be coupled to each other by any of the numerous known internucleoside linkages. Such internucleoside linkages include without limitation phosphorothioate, phosphorodithioate, alkylphosphonate, alkylphosphonothioate, phosphotriester, phosphoramidate, siloxane, carbonate, carboxymethylester, acetamidate, carbamate, thioether, bridged phosphoramidate, bridged methylene phosphonate, bridged phosphorothioate and sulfone internucleotide linkages. In certain preferred embodiments, these internucleoside linkages may be phosphodiester, phosphotriester, phosphorothioate, or phosphoramidate linkages, or combinations thereof. The term oligonucleotide also encompasses such polymers having chemically modified bases or sugars and/or having additional substituents, including without limitation lipophilic groups, intercalating agents, diamines and adamantane. For purposes of the invention the term "2'-O-substituted" means substitution of the 2' position of the pentose moiety with an -O-lower alkyl group containing 1–6 saturated or unsaturated carbon atoms, or with an -O-aryl or allyl group having 2–6 carbon atoms, wherein such alkyl, aryl or allyl group may be unsubstituted or may be substituted, e.g., with halo, hydroxy, trifluoromethyl, cyano, nitro, acyl, acyloxy, alkoxy, carboxyl, carbalkoxyl, or amino groups; or such 2' substitution may be with a hydroxy group (to produce a ribonucleoside), an amino or a halo group, but not with a 2'-H group.

Particularly preferred antisense oligonucleotides according to this aspect of the invention include chimeric oligonucleotides and hybrid oligonucleotides.

For purposes of the invention, a "chimeric oligonucleotide" refers to an oligonucleotide having more than one type of internucleoside linkage. One preferred embodiment of such a chimeric oligonucleotide is a chimeric oligonucleotide comprising a phosphorothioate, phosphodiester or phosphorodithioate region, preferably comprising from about 2 to about 12 nucleotides, and an alkylphosphonate or alkylphosphonothioate region. Preferably, such chimeric oligonucleotides contain at least three consecutive internucleoside linkages selected from phosphodiester and phosphorothioate linkages, or combinations thereof.

For purposes of the invention, a "hybrid oligonucleotide" refers to an oligonucleotide having more than one type of nucleoside. One preferred embodiment of such a hybrid oligonucleotide comprises a ribonucleotide or 2'-O-substituted ribonucleotide region, preferably comprising from about 2 to about 12 2'-O-substituted nucleotides, and a deoxyribonucleotide region. Preferably, such a hybrid oligonucleotide will contain at least three consecutive deoxyribonucleosides and will also contain ribonucleosides, 2'-O-substituted ribonucleosides, or combinations thereof.

The exact nucleotide sequence and chemical structure of an antisense oligonucleotide according to the invention can be varied, so long as the oligonucleotide retains its ability to inhibit DNA MeTase expression. This is readily determined by testing whether the particular antisense oligonucleotide is active in a DNA MeTase enzyme assay, a soft agar growth assay, or an in vivo tumor growth assay, all of which are described in detail in this specification.

Antisense oligonucleotides according to the invention may conveniently be synthesized on a suitable solid support using well known chemical approaches, including H-phosphonate chemistry, phosphoramidite chemistry, or a combination of H-phosphonate chemistry and phosphoramidite chemistry (i.e., H-phosphonate chemistry for some cycles and phosphoramidite chemistry for other cycles). Suitable solid supports include any of the standard solid supports used for solid phase oligonucleotide synthesis, such as controlled-pore glass (CPG). (See, e.g., Pon, Methods in Molec. Biol. 20: 465 (1993)).

Antisense oligonucleotides according to the invention are useful for a variety of purposes. For example, they can be used as "probes" of the physiological function of DNA MeTase by being used to inhibit the activity of DNA methyltransferase in an experimental cell culture or animal system and to evaluate the effect of inhibiting such DNA MeTase activity. This is accomplished by administering to a cell or an animal an antisense oligonucleotide according to the invention and observing any phenotypic effects. In this use, antisense oligonucleotides according to the invention are preferable to traditional "gene knockout" approaches because they are easier to use and can be used to inhibit DNA MeTase activity at selected stages of development or differentiation. Thus, antisense oligonucleotides according to the invention can serve as probes to test the role of DNA methylation in various stages of development.

Finally, antisense oligonucleotides according to the invention are useful in therapeutic approaches to benign and malignant tumors and other human diseases involving suppression of gene expression. The anti-tumor utility of antisense oligonucleotides according to the invention is described in detail elsewhere in this specification. In addition, antisense oligonucleotides according to the invention may be used to activate silenced genes to provide a missing gene function and thus ameliorate disease symptoms. For example, the diseases beta thalassemia and sickle cell anemia are caused by aberrant expression of the adult beta globin gene. Most individuals suffering from these diseases have normal copies of the fetal gene for beta globin. However, the fetal gene is hypermethylated and is silent. Activation of the fetal globin gene could provide the needed globin function, thus ameliorating the disease symptoms.

For therapeutic use, antisense oligonucleotides according to the invention may optionally be formulated with any of the well known pharmaceutically acceptable carriers or diluents. This formulation may further contain one or more DNA MeTase inhibitor and/or one or more additional anti-DNA MeTase antisense oligonucleotide or it may contain any other pharmacologically active agent.

In a fourth aspect, the invention provides a method for investigating the role of DNA MeTase in cellular growth, including the growth of tumor cells. In the method according to this aspect of the invention, the cell type of interest is contacted with an antisense oligonucleotide according to the invention, resulting in inhibition of expression of DNA MeTase in the cell. The antisense oligonucleotides can be administered at different points in the cell cycle, or in conjunction with promoters or inhibitors of cell growth to determine the role of DNA MeTase in the growth of the cell type of interest.

In a fifth aspect, the invention provides methods for inhibiting tumor growth comprising administering to an animal, including a human, antisense oligonucleotides according to the invention. In the method according to this aspect of the invention a therapeutically effective amount of an antisense oligonucleotide according to the invention is administered for a therapeutically effective period of time to an animal, including a human, which has at least one tumor cell present in its body.

As used herein the term "tumor growth" is used to refer to the growth of a tumor cell. A "tumor cell" is a neoplastic cell. A tumor cell may be benign, i.e. one that does not form metastases and does not invade and destroy adjacent normal tissue, or malignant, i.e. one that invades surrounding tissues, is capable of producing metastases, may recur after attempted removal, and is likely to cause death of the host.

The terms "therapeutically effective amount" and "therapeutically effective period of time" are used to denote known treatments at dosages and for periods of time effective to reduce tumor cell growth. Preferably, such administration should be parenteral, oral, sublingual, transdermal, topical, intranasal or intrarectal. When administered systemically, the therapeutic composition is preferably administered at a sufficient dosage to attain a blood level of antisense oligonucleotide from about 0.01 μM to about 10 μM. For localized administration, much lower concentrations than this may be effective, and much higher concentrations may be tolerated. Preferably, a total dosage of DNA MeTase inhibitor will range from about 0.1 mg oligonucleotide per patient per day to about 200 mg oligonucleotide per kg body weight per day.

According to another embodiment, one or more of the oligonucleotides of the invention may be administered to an animal this aspect of the invention provides methods for inhibiting tumor growth comprising administering to an animal, including a human, more than one antisense oligonucleotide according to the invention either sequentially or simultaneously in a therapeutically effective amount and for a therapeutically effective period of time.

The following examples are intended to further illustrate certain preferred embodiments of the invention and are not limiting in nature.

EXAMPLE 1

Inhibition of DNA MeTase Expression As Measured in Nuclear Extracts Prepared from Human or Murine Cells Nuclear extracts are prepared from 1×10$^8$ mid-log phase human H446 cells or mouse Y1 cells which have been grown under standard cell culture conditions. Cells were treated with medium supplemented with 1 mg/ml of an antisense oligonucleotide complementary to a noncoding region of the DNA MeTase RNA transcript or a randomer (negative control) oligonucleotide. The cells are harvested and washed twice with phosphate buffered saline (PBS), then the cell pellet is resuspended in 0.5 ml Buffer A (10 mM Tris pH 8.0, 1.5 mM $MgCl_2$, 5 mM $KCl_2$, 0.5 mM DTT, 0.5 mM PMSF and 0.5% Nonidet P40) to separate the nuclei from other cell components. The nuclei are pelleted by centrifugation in an Eppendorf microfuge at 2,000 RPM for 15 min at 4° C. The nuclei are washed once in Buffer A and re-pelleted, then resuspended in 0.5 ml Buffer B (20 mM Tris pH 8.0, 0.25% glycerol, 1.5 mM $MgCl_2$, 0.5 mM PMSF, 0.2 mM EDTA 0.5 mM DTT and 0.4 mM NaCl). The resuspended nuclei are incubated on ice for 15 minutes then spun at 15,000 RPM to pellet nuclear debris. The nuclear extract in the supernatant is separated from the pellet and used for assays for DNA MeTase activity. For each assay, carried out in triplicate, 3 μg of nuclear extract is used in a reaction mixture containing 0.1 μg of a synthetic 33-base pair hemimethylated DNA molecule substrate with 0.5 μCi S-[methyl-$^3$H] adenosyl-L-methionine (78.9 Ci/mmol) as the methyl donor in a buffer containing 20 mM Tris-HCl (pH 7.4), 10 mM EDTA, 25% glycerol, 0.2 mM PMSF, and 20 mM 2-mercaptoethanol. The reaction mixture is incubated for 1 hour at 37° C. to measure the initial rate of the DNA MeTase. The reaction is stopped by adding 10% TCA to precipitate the DNA, then the samples are incubated at 4° C. for 1 hour and the TCA precipitates are washed through GFC filters (Fischer, Hampton, N.H.). Controls are DNA incubated in the reaction mixture in the absence of nuclear extract, and nuclear extract incubated in the reaction mixture in the absence of DNA. The filters are laid in scintillation vials containing 5 ml of scintillation cocktail and tritiated methyl groups incorporated into the DNA are counted in a β-scintillation counter according to standard methods. To measure inhibition of DNA MeTase expression, the specific activity of the nuclear extract from oligonucleotide-treated cells is compared with the specific activity of the extract from untreated cells. Treatment of cells with antisense oligonucleotides of the invention results in reduction in DNA MeTase activity in the nuclear extract.

EXAMPLE 2

Antisense Oligonucleotide Accumulation in Cells

Antisense oligonucleotides are labeled with $^{32}$P using standard procedures. 300,000 Y1 cells per well are plated in a six-well tissue culture plate. Labeled antisense oligonucleotides are added to a final concentration of 1 μM. Cells are harvested at different time points by trypsinization according to methods well known in the art, and washed extensively with PBS to remove nonincorporated compounds. The cell pellet is resuspended in 20 μl buffer RIPA (0.5% deoxycholic acid, 0.1% SDS, 1% NP-40, in PBS). The homogenate is incubated at 4° C. for 30 minutes, then spun in a microfuge at maximum speed for 30 minutes, after which the supernatant is transferred to a new tube. Two μl of supernatant are extracted with phenol-chloroform by adding 1 μl of phenol and 1 μl of chloroform, the suspension is mixed and the organic and aqueous phases are separated by centrifugation in a microfuge for 10 minutes at 15,000 RPM. The aqueous phase is extracted and loaded onto a 20% polyacrylamide-urea gel. Visualization is by autoradiography. The results demonstrate that antisense oligonucleotides are taken up by the cells in a time-dependent manner.

EXAMPLE 3

Analysis of Cellular DNA Methylation in Cells Treated with Antisense Oligonucleotides Nuclear extracts are prepared from randomer oligonucleotide-treated cells and from antisense oligonucleotide-treated cells (1 μM oligonucleotide) as described in Example 1. The DNA pellet is resuspended in 0.5 ml DNA extraction buffer (0.15M NaCl, 1% SDS, 20 mM Tris-HCl pH 8.0, 5 mM EDTA), 100 Mg Proteinase K is added, and the suspension is incubated at 50° C. for 16 hours. The DNA is extracted in phenol-chloroform by adding 0.25 ml phenol and 0.25 ml chloroform. The suspension is mixed and the organic and aqueous phases are separated by centrifugation in a microfuge for 10 minutes at 15,000 RPM. One ml absolute ethanol is added to the aqueous phase and the DNA is precipitated by centrifugation in a microfuge for 15 minutes at 15,000 RPM. The DNA pellet is washed in 70% ethanol and re-pelleted by centrifugation. The DNA is resuspended in 100 μl 20 mM Tris-HCl pH 8.0, 1 mM EDTA.

Two μg DNA are incubated at 37° C. for 15 minutes with 0.1 unit of DNase, 2.5 μl $^{32}$P-α-dGTP (3000 Ci/mmol, Amersham, (Cleveland, Ohio) and then 2 units Kornberg DNA Polymerase (Boehringer Mannheim, Mannheim, Germany) are added and the reaction mixture is incubated for an additional 25 minutes at 30° C. Fifty μl $H_2O$ are then added and nonincorporated radioactivity is removed by spinning through a Microspin S-300 HR column (Pharmacia, Piscataway, N.J.). Labelled DNA (20 μl) is digested with 70 μg micrococcal nuclease (Pharmacia, Piscataway, N.J.) in the manufacturer's recommended buffer for 10 hours at 37° C. Equal amounts of radioactivity are loaded onto TLC phosphocellulose plates (Merck, Darmstadt, Germany) and the 3' mononucleotides are separated by chromatography in one direction, in 66:33:1 isobutyric acid/H$_2$O/NH$_4$OH. The chromatograms are exposed to XAR film (Eastman Kodak, Rochester, N.Y.) and the autoradiograms are scanned by laser densitometry (Scanalytics, CSPI, Billerica, Mass.). Spots corresponding to cytosine and 5-methylcytosine are quantified and the percentage of non-methylated CG dinucleotides is determined. The results are expected to demonstrate an overall reduction in the percentage of non-methylated CG dinucleotides in antisense oligonucleotide-treated cells, relative to randomer-treated cells.

To assess demethylation of specific genes, a procedure is carried out as generally described in J. Biol. Chem. 270: 12690–12696 (1995). Briefly, the genomic DNA (10 μg) is extracted and subjected to digestion by 25 units HindIII, followed by digestion by either 25 units MspI (CG methylation insensitive) or 25 units HpaII (CG methylation sensitive) for 8 hours at 37° C. The digested DNA is separated on a 1.5% agarose gel and subjected to Southern blotting and hybridization with specific probes. The results are expected to show that genes which are ordinarily heavily methylated in the test cells become undermethylated, whereas the methylation levels for genes which are not ordinarily heavily methylated in the test cells are not significantly affected.

EXAMPLE 4

Inhibition of Tumor Growth By Antisense Oligonucleotides

Y1 or H446 cells are plated on a 6 well plate at a density of 80,000 cells/well. Antisense oligonucleotide phosphorothioates complementary to a DNA MeTase noncoding region (about 0.5 to 20 μM) are added to the cells. The cells are similarly treated daily for 7 days. Then, the cells are harvested and 3,000 live cells are plated in soft agar, for example, as described in Freedman and Shin, Cell 3: 355–359 (1974). Two weeks after plating, the number of colonies formed in soft agar are scored by visual examination. In the case of active antisense oligonucleotides, a dose-dependent reduction in the number of colonies is observed.

Alternatively, 6 to 8 week old LAF-1 mice (Jackson Labs, Bar Harbor, Me.) are injected subcutaneously in the flank area with 2×10$^6$ Y1 cells. Three days later, the mice are injected with 1–5 mg/kg antisense oligonucleotide phosphorothioates complementary to a DNA MeTase noncoding region. This dosing is repeated every two days. After one month, the mice are sacrificed and the tumor size is determined according to standard protocols. (see e.g., Ramchandani et al. Proc. Natl. Acad. SCI. USA 94: 684–689 (1997) In the case of active antisense oligonucleotides, significant reduction in tumor size is observed, relative to controls treated with a randomized or a reverse antisense sequence.

EXAMPLE 5

Affinity Binding of DNA MeTase Enzyme

To demonstrate affinity binding of DNA MeTase enzyme, a binding substrate hairpin oligonucleotide having the sequence
5'-CTGAAmCGGATmCGTTTCGATCUGTTCAG-3' (SEQ ID NO: 71) was provided at 4 μM concentration. The hairpin oligonucleotide was labeled using polynucleotide kinase and gamma $^{32}$P-γ-ATP (300 mCi/mmol, 50 μCi) (New England Biolabs, Beverly, Mass.) as recommended by the manufacturer. Labeled oligonucleotide was separated from nonincorporated radioactivity by passing through a G-50 Sephadex spin column (Pharmacia, Uppsala, Sweden). Labeled hairpin oligonucleotide (500 nM) was incubated with 5 μg nuclear extract prepared as described in Example 1. The incubation, in the same buffer used for the DNA MeTase activity assay, was at 37° C. for 30 minutes. To determine whether complex formation was dependent on the cofactor SAM, the reaction was carried out both in the presence and the absence of SAM). Then, loading dye (0.3M Tris-HCl pH 8.8, 0.2% SDS, 10% glycerol, 28 mM 2-mercaptoethanol and 24 μg/ml bromophenol blue) was added and the sample was separated on a 5% SDS-polyacrylamide gel (SDS-PAGE) with a 4% stacking gel according to standard procedures. Following SDS-PAGE separation, the gel was exposed to autoradiography for visualization of a complex migrating at 190 kDa. Alternatively, the gel was electrotransferred onto a PVDF membrane (Amersham Life Sciences, Buckinghamshire, England) using a electrotransfer apparatus (BioRad, Hercules, Calif.) at 250 milliamperes for 2.5 hours in electrotransfer buffer (3.03 g/l Tris base, 14.4 g/l glycine, 1 g/l SDS, pH 8.3) for Western blotting with a DNA MeTase-specific antisera. The membrane was blocked for 1 hour in a buffer containing 5 mm Tris base, 200 mM NaCl, 0.5% Tween-20 and 5% dry milk. Rabbit antisera was raised according to standard procedures (see e.g., *Molecular Cloning*, 2d Edition, Cold Spring Harbor Laboratory Press (1989)) against a peptide sequence found in the catalytic domain of human and murine DNA MeTase (amino acids GQRLPQKGDVENLKGGPPC; SEQ ID NO: 72). The antisera was added to the membrane at a 1:200 dilution and incubated for 1 hour. The membrane was washed with the blocking buffer, then reacted with a 1:5000 dilution of goat anti-rabbit secondary antibody (Amersham, Cleveland, Ohio) for an additional hour. The membrane was then washed for 10 minutes in blocking buffer, three times, and bands reacting with anti-DNA MeTase antibody were visualized using an ECL detection kit according to the manufacturer protocols (Amersham, Cleveland, Ohio).

The results demonstrated that a 190 kDa complex is detected by both autoradiography and Western blotting (see FIG. 2), strongly indicating that the 190 kDa complex is formed between the hairpin oligonucleotide and DNA MeTase enzyme. Subsequent experiments using antisera raised against another peptide sequence found in the catalytic domain of human and murine DNA MeTase (amino acids GGPPCQGFSGMNRFNSRTY; SEQ ID NO: 73) (see, Ramchandani et al. supra) confirmed the same results. These results further demonstrated that such complex formation is independent of the cofactor SAM since none was present. Furthermore, data showed that complex formation is achieved within 30 minutes, thus suggesting that such complex formation provides an assay for the level of DNA MeTase in different cell samples and a method to purify methyltransferase by affinity binding.

EXAMPLE 6

Analysis of Treated Cells

Enzymatic activity profiles were performed to quantitate the ability of the synthetic oligonucleotides of the present invention to inhibit DNA methyltransferase expression. A549 cells (ATCC), and T24 cells (ATCC) were grown according to standard cell culture techniques. Cells were then treated for 24 hours with growth medium containing 250 nM of an antisense oligonucleotide complementary to a special target region of the DNA MeTase RNA transcript or a scrambled (negative control) oligonucleotide, and 10 µg/ml lipofectin.

Cells were then harvested and washed twice with PBS and the nuclei were pelleted by centrifugation in an Eppendorf microfuge at 2,000 RPM for 15 min at 4° C. The nuclei were washed once in Buffer A and re-pelleted, then resuspended in 0.5 ml Buffer B (20 mM Tris pH 8.0, 0.25% glycerol, 1.5 mM $MgCl_2$, 0.5 mM PMSF, 0.2 mM EDTA 0.5 mM DTT and 0.4 mM NaCl). The resuspended nuclei were incubated on ice for 15 minutes then spun at 15,000 RPM to pellet nuclear debris. The nuclear extract in the supernatant was separated from the pellet and used for assays for DNA MeTase activity. For each assay, carried out in triplicate, 3 µg of nuclear extract was used in a reaction mixture containing 0.1 µg of a synthetic 33-base pair hemimethylated DNA molecule substrate with 0.5 µCi S-[methyl-$^3$H] adenosyl-L-methionine (78.9 Ci/mmol) as the methyl donor in a buffer containing 20 mM Tris-HCl (pH 7.4), 10 mM EDTA, 25% glycerol, 0.2 mM PMSF, and 20 mM 2-mercaptoethanol. The reaction mixture was incubated for 1 hour at 37° C. to measure the initial rate of the DNA MeTase. The reaction was stopped by adding 10% TCA to precipitate the DNA, then the samples were incubated at 4° C. for 1 hour and the TCA precipitates were washed through GFC filters (Fischer). Control were DNA samples incubated in the reaction mixture in the absence of nuclear extract, and nuclear extract incubated in the reaction mixture in the absence of DNA. The filters were laid in scintillation vials containing 5 ml of scintillation cocktail and tritiated methyl groups incorporated into the DNA are counted in a β-scintillation counter according to standard methods. To normalize and thus compare specific activity of the nuclear extracts from cells treated with various synthetic oligonucleotide both DNA MeTase and G3PDH activity were measured. FIG. 3 shows DNA MeTase enzymatic activity observed in A549 cells treated with 26 different synthetic oligonucleotides as indicated. Similar results were observed when using T24 cells. Note that values were expressed as a percentage of activity observed in cells treated with scrambled synthetic oligonucleotides. The results show that the treatment of cells with antisense oligonucleotides of the invention results in reduction in DNA MeTase activity in the nuclear extracts.

EXAMPLE 7

Inhibition of Tumor Growth in Vivo

Ten to twelve week old female BALB/c nude mice (Taconic Labs, Great Barrington, N.Y.) were injected subcutaneously in the flank area with $2 \times 10^6$ preconditioned A549 human lung carcinoma cells. Preconditioning of these cells was done by a minimum of three consecutive tumor transplantations in the same strain of nude mice. Subsequently, tumor fragments of approximately 25 mgs were excised and implanted subcutaneously in mice, in the left flank area under Forene anestesia (Abbott Labs., Geneva, Switzerland). When the tumors reached a mean volume of 100 $mm^3$, the mice were treated intravenously, by daily bolous infusion into the tail vein, with oligonucleotide saline preparations containing 2 mg/Kg of oligonucleotide according to the present invention. The optimal final concentration of the oligonucleotide is established by dose response experiments according to standard protocols. Tumor volume was calculated according to standard methods every second day post infusion. (e.g., Meyer et al. Int. J. Cancer 43:851–856 (1989)). Treatment with the oligonucleotides of the invention caused a significant reduction in tumor weight and volume relative to controls treated with randomized or reverse antisense sequence (data not shown). In addition, the activity of DNA MeTase enzyme was measured and found to be significantly reduced relative to randomer treated controls. These results show that the oligonucleotides according to the invention are capable of inhibiting MeTase enzymatic activity and tumor growth.

EXAMPLE 8

DNA MeTase Gene Organization and Structure

Figure 4A:
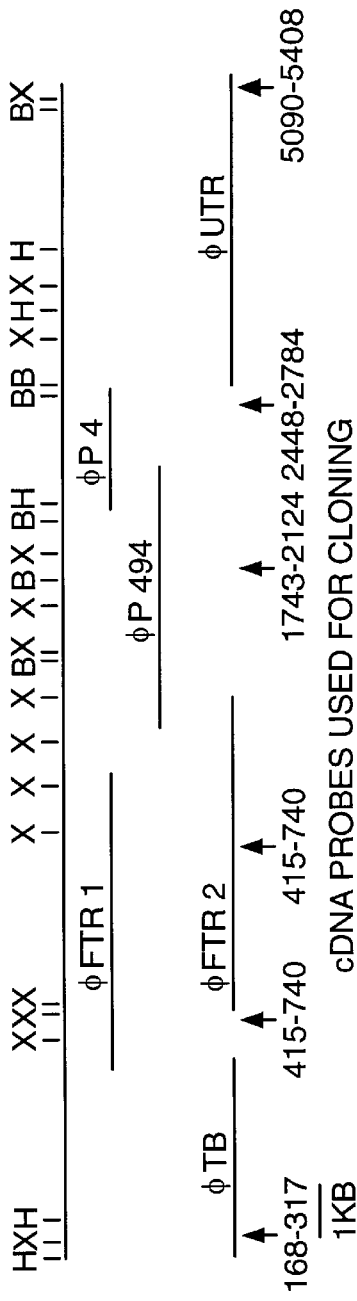
FIGS. 4A–4C: Panel (A) shows the restriction map and phage clones of the human DNA MeTase gene. The cDNA probes used for screening are indicated by arrows under the lines representing the genomic fragments contained in the phages (the name of each phage is indicated above the line) identified by each of the probes. The numbers under the arrow indicate the 5' and 3' ends of the cDNA sequences included in each of the probes. The cDNA is numbered as in Yoder et al., 1996. Genomic inserts were isolated from the phages by NotI digestion and sub-cloned into NotI linearized pBluescript SK+. Sub-clones were digested with restriction endonucleases (X=Xba 1, B=Bam H1, H=Hind III) Southern blotted and hybridized to exon specific $^{32}$P labelled oligodeoxyribonucleotides or cDNA probes to produce a scale restriction map of the human DNA MeTase gene.
Figure 4B:
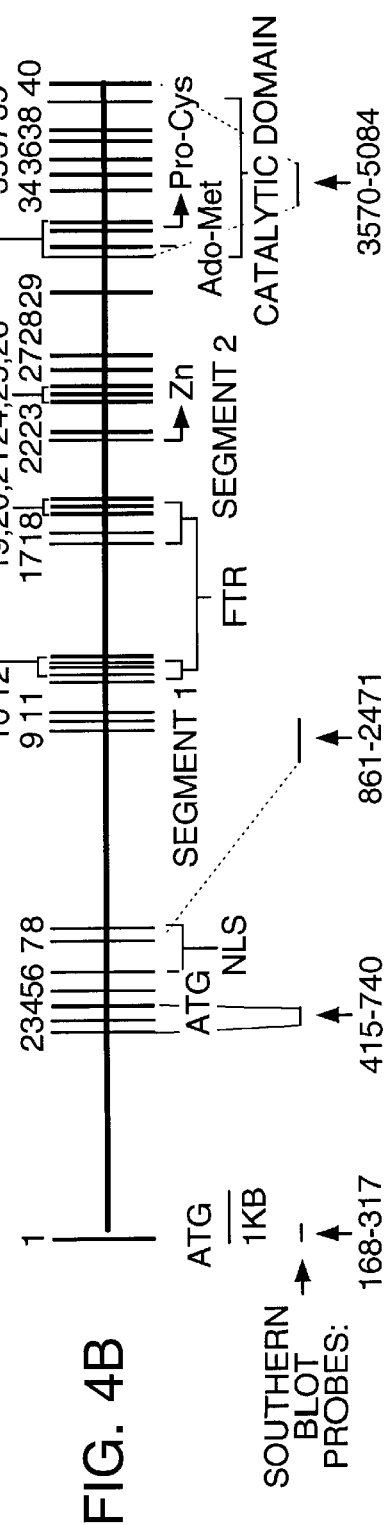
Figure 4C:
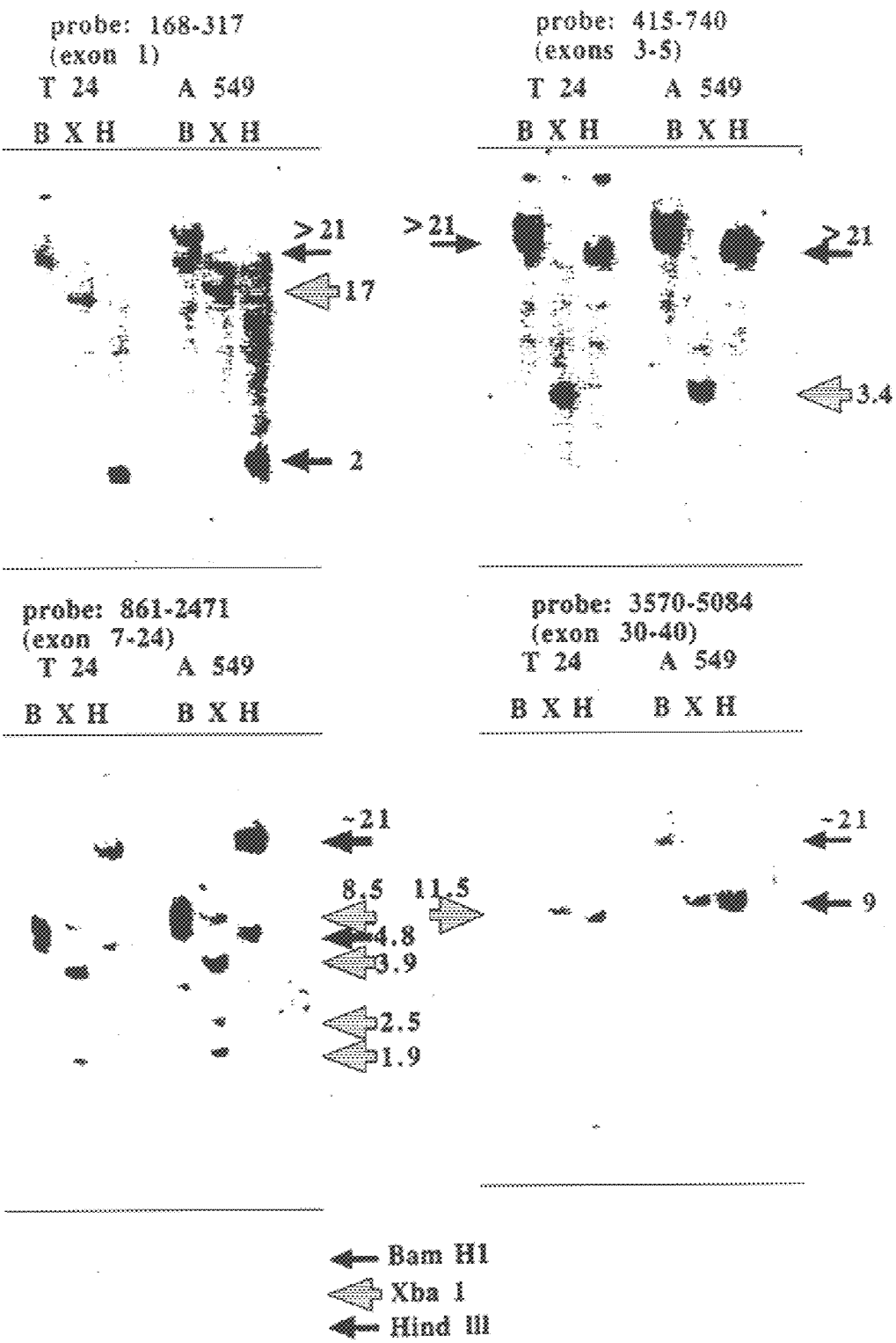

Information regarding the chromosomal organization of the human DNA MeTase gene is useful for (a) a comprehensive analysis of the mechanisms that underlie the regulation of DNA MeTase expression in oncogenic progression and developmental processes (e.g., analysis of potential alternative splicing products, regulatory elements such as enhancers and promoters reside in intronic genomic regions), and (b) for designing antisense oligodeoxyribonucleotides according to the invention. In order to obtain overlapping DNA fragments spanning the entire human DNA MeTase gene, several cDNA fragments spanning the known human DNA MeTase cDNA were generated via RT-PCR (mRNA source Hela and A549 cells) (FIG. 4A) and used as probes to screen human genomic DNA libraries from lung and placenta, in Lambda FIX II (Stratagene). The cDNA probes spanned the entire known human cDNA sequence (Yen et al., 1992 and Yoder et al., 1996). Genomic inserts were isolated from the phages by NotI digestion and sub-cloned into NotI linearized pBluescript SK+. Sub-clones were digested with restriction endonucleases (X=Xba 1, B=Bam H1, H=Hind III) Southern blotted and hybridized to exon specific $^{32}$P labelled oligodeoxyribonucleotides or cDNA probes to produce a scale restriction map of the human DNA MeTase gene. Sub-clones were exon sequenced to determine exon-intron boundaries. Intron sizes were determined by either DNA sequencing (for introns less than 150 bp), PCR using 5' and 3' flanking exon sequences as primer sources (for introns less than 2 Kb) and restriction enzyme-Southern blot analysis using the enzymes indicated in A (data not shown) using oligonucleotides for each specific exon to verify the restriction enzyme. For larger introns (>2 kb), the distance between the exons was estimated by restriction enzyme analysis of phage insert and mapping the exons to the different restriction fragments using exon specific oligonucleotide probes (see physical map in FIG. 4A) The physical map obtained by restriction enzyme analysis of phage DNA (FIG. 4A) was verified by a restriction enzyme-Southern blot analysis of human genomic DNA. Genomic DNA was prepared as described previously (Sambrook et al. 1989) from human lung carcinoma A549 cells (ATCC: CCL-185) and human bladder carcinoma cells: T24 (ATCC: HTB-4) and digested with restriction endonucleases Xba 1 (X), Bam H1 (B), or Hind III (H), electrophoresed on a 1.5% agarose gel and Southern blotted. The fragments encoding the different segments of the human DNA MeTase mRNA were visualized by hybridization to the following cDNA probes: 1. A probe bearing the first exon. 2. A probe bearing exons 3–5 (starting spanning nucleotides 415–740 of the known cDNA) 3. A probe bearing exons 7–20 4. A probe spanning exons 30–40. The cDNA probes are indicated under the map of the exon-intron structure, the dashed lines delineate the boundaries of exons spanned by each of the probes. The fragments visualized by each of the restriction enzymes are indicated by different shaded arrows. The size of the visualized fragments is indicated next to the arrows. The size of the fragments visualized by each of the probes corresponds to the size predicted by the restriction enzyme analysis of the genomic phages. The fragments predicted by the physical map of the different phages (FIG. 4A) were visualized with the cDNA probes in the Southern blots of genomic DNA (FIG. 4C, arrows indicate the restriction enzyme fragments, and their sizes, visualized with each cDNA probe). The positions of exons determined by PCR analysis were verified by Southern blot analysis. The following primers were used to map by PCR the relevant intron boundaries and sizes: exons 4 to 5: sense: 5'-aaacgggaaccaagcaagaa (SEQ ID NO: 74); antisense: 5'-tgagatgtgatggtggttt (SEQ ID NO: 75); exons 5 to 6: sense: 5'-ctgaaccttcacctagcccc (SEQ ID NO: 76); antisense: gatggactcatccgatttgg (SEQ ID NO: 77); exons 6 to 7: sense: 5'-ccctgccaaacggaaacctc (SEQ ID NO: 78); antisense: 5'-gttctctggatgtaactcta (SEQ ID NO: 79); exons 7 to 8: sense: agacgtagagttacatccag (SEQ ID NO: 80); antisense: 5'-gctctttcaggttcttctgc (SEQ ID NO: 81); exons 9 to 10: sense: 5'-aagaaaagagactccgaagt (SEQ ID NO: 82); antisense: tttctcgtctccatcttcgt (SEQ ID NO: 83); exons 10 to 11: sense: 5'-gtcagcccttaggagctgtt (SEQ ID NO: 84); antisense: 5'-ggaaacagctatgaccatg ((SEQ ID NO: 85; M13 reverse primer); exons 11 to 12: sense: 5'-gatgagaagaagcacagaag (SEQ ID NO: 86); antisense 5'-tcatcctcgtcttttcatcagaa (SEQ ID NO: 87); exons 12 to 13: sense: 5'-ttctgatgaaaaagacgaggatga (SEQ ID NO: 88); antisense: 5'-cattaccatctgctttggat (SEQ ID NO: 89); exons 13 to 14: sense: 5'-aggagaagagacgcaaaacg (SEQ ID NO: 90); antisense: 5'-agttcatgactgttttggcg (SEQ ID NO: 91); exons 17 to 18; sense: 5'-gtactgtaagcacggtcacc (SEQ ID NO: 92); antisense: 5-aggtgctgaagccgatgagg (SEQ ID NO: 93); exons 18 to 19: sense: 5'-tggatcactggctttgatgg (SEQ ID NO: 94); antisense: 5'-ctcgatcttgttgatcaggt (SEQ ID NO: 95); exons 21 to 22: sense: 5'-aggcgagcccaggcgaggcg (SEQ ID NO: 96); antisense: 5'-cgctcttggcaagcctgcttg (SEQ ID NO: 97); exons 22 to 23: sense: 5'-gtgtcagcagcctgagtgtg (SEQ ID NO: 98); antisense: 5'-ctccgacccaagagatgcga (SEQ ID NO: 99); exons 23 to 24: sense: gtcccaatatggccatgaag (SEQ ID NO: 100); antisense: 5'-gctagatacagcggttttgagg (SEQ ID NO: 101); exons 24 to 25: sense: 5'-cgtcaagactgatgggaagaagagt (SEQ ID NO: 102); antisense: 5'-ctccatggcccagttttcgg (SEQ ID NO: 103); exons 25 to 26: sense: 5'-gtcacggcgctgtgggagga (SEQ ID NO: 104); antisense: 5'-ttgaacttgttgtcctctgt (SEQ ID NO: 105); exons 26 to 27: sense: 5'-gacctacttctaccagctgt (SEQ ID NO: 106); antisense: 5-ttgaacgtgaaggcctcagg (SEQ ID NO: 107); exons 27 to 28: sense: 5'-ctctactactcagccaccaa (SEQ ID NO: 108); antisense: 5'-tagaacttgttgacccgga (SEQ ID NO: 109); exons 28 to 29: sense: 5'-tgagactgacatcaaaatcc (SEQ ID NO: 110); antisense: 5'-cgaggaagtagaagcggtg (SEQ ID NO: 111); exons 29 to 30: sense: 5'-cgagtgcgtccaggtgtact (SEQ ID NO: 112); antisense: 5'-cttccctttgtttccagggc (SEQ ID NO: 113); exons 31 to 32: sense: 5'-gaagggcaagcccaagtcc (SEQ ID NO: 114); antisense: 5'-agccatgaccagcttcagca (SEQ ID NO: 115); exons 32 to 33: sense: 5'-tgctgaagctggtcatggct (SEQ ID NO: 116); antisense: 5'-cctgcagcacgccgaaggtg (SEQ ID NO: 117); exons 33 to 34: sense: 5'-tccttcaagcgctccatggt (SEQ ID NO: 118); antisense: 5'-tagtctgggccacgccgtac (SEQ ID NO: 119); exons 34 to 35: sense: 5'-ccggtcagtacggcgtggcc (SEQ ID NO: 120); antisense: 5'-agatctccagtgccgaggct (SEQ ID NO: 121); exons 35 to 36: sense: 5'-tgagctcgggtccttccgg (SEQ ID NO: 122); antisense: 5'-tccacgcaggagcagacccc (SEQ ID NO: 123); exons 36 to 37: sense: 5'-tcagacggcaccatggccag (SEQ ID NO: 124); antisense: 5'-cttgcccatgggctcggggt (SEQ ID NO: 125); exons 37 to 38: sense: 5'-ctctatggaaggctcgagtg (SEQ ID NO: 126); antisense: 5'-cggtgcttgtccaggatgtt (SEQ ID NO: 127); exons 38 to 39: sense: 5'-ctgacacctaccggctcttc (SEQ ID NO: 128); antisense: 5'-ggcactctctcgggcttttgg (SEQ ID NO: 129); exons 39 to 40: sense: 5'-ggagatcaagctttgtatgt (SEQ ID NO: 130); antisense: 5'-gtccttagcagcttcctcct (SEQ ID NO: 131). The following introns were determined by sequencing: exons 2 to 3; 3 to 4; 14 to 15; 15 to 16; 19 to 20; 20 to 21; 30 to 31. The following introns were determined by restriction mapping: exons 1 to 2 (using the following oligonucleotides as probes: exon 1: 5'-cgcctgcggacatcgtcgggcagc (SEQ ID NO: 132); T3: 5'-aattaaccctcactaaaggg (SEQ ID NO: 133); T7: 5'-gtaatacgactcactatagggc (SEQ ID NO: 134)) ; 8 to 9 (using the following oligonucleotides as probes: exon 8: 5'-gctctttcaggttcttctgc (SEQ ID NO: 135); exon 9: 5'-aagaaaagagactccgaagt (SEQ ID NO: 136)); 16 to 17 (using the following oligonucleotides as probes: exon 16: 5'-tgagccacagatgctgacaaa (SEQ ID NO: 137); exon 17: 5'-gtactgtaagcacggtcacc (SEQ ID NO: 138)). The results of the cloning, sequencing and mapping experiments demonstrate that the 5.2 kilobase cDNA for the human DNA MeTase, is organised as 40 exons and 39 introns, with completely conserved splice acceptor and donor sites (FIG. 5), on 60 kilobases of chromosome 19p13.2–13.3 (FIG. 4B). This gene can therefore be classified as a "large gene" similar to Rb (70 kb) and apolipoprotein B (79.5 kb).

The functional domains of the DNA MeTase appear to be grouped together as a number of small exons and introns separated from neighbouring domains by large introns (FIG. 4B). First, exons 6–8 code for the nuclear localization signal and exist within an isolated cluster that contains exons 2–8 and flanked by the large introns 1 and 8 (12 and 11 kilobases respectively). Second, the region described to be critical for targeting of the enzyme to replication foci (FTR) is coded for by exons 13–20. These exons are organized into two distinct chromosomal regions, exons 13–16 make up the first region, and exons 17–20 make up the second, and are separated by the large intron 16 (6000 bases). Third, the region responsible for zinc binding is coded for by exon 22, and in its genomic organization, along with exon 23, is isolated by the large flanking introns 21 and 23. Fourth, the catalytic domain of the enzyme is coded for by exons 30–39. The catalytic domain of all of the known CpG methyltransferases share 10 conserved motifs of which 1,4,6,8,9, and 10 appear to be essential for catalytic activity. Conserved motif 1 is entirely contained within exon 31 and codes for the AdoMet binding peptide. Conserved motif 4 is entirely contained within exon 32 and contains the Pro-Cys motif that catalyzes methyl transfer. Fifth, two postulated translation initiation codons exist (FIG. 4B) and the genomic organization of the exons in which they reside suggests that they form distinctly different structural motifs. The antisense oligonucleotide of the invention hybridize to the target intron-exon boundary by Watson and Crick hybridization and effectively mask the splice junction. There is confidence that this approach can be successfully exploited for DNA MeTase because the gene offers 78 unique intron-exon junctions (FIG. 5) for antisense oligonucleotide development.

What is claimed is:

1. An oligonucleotide which inhibits DNA methyltransferase expression, the oligonucleotide having from 8 to 100 nucleotides and being complementary to a region of an RNA that encodes DNA methyltransferase, wherein the region includes 2 to 50 nucleotides selected from the group consisting of the nucleotide sequences set forth in the Sequence Listings as SEQ ID NO 1, SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 22, SEQ ID NO 23, SEQ ID NO 24, SEQ ID NO 25, SEQ ID NO 26, SEQ ID NO 27, SEQ ID NO 28, SEQ ID NO 29, SEQ ID NO 30, SEQ ID NO 31, SEQ ID NO 32, SEQ ID NO 33, SEQ ID NO 34, SEQ ID NO 35, SEQ ID NO 36, SEQ ID NO 37, and SEQ ID NO 38.

2. The oligonucleotide according to claim 1, wherein the oligonucleotide has at least one internucleotide linkage selected from the group consisting of phosphorothioate, phosphorodithioate, alkylphosphonate, alkylphosphonothioate, phosphotriester, phosphoramidate, siloxane, carbonate, carboxymethylester, acetamide, carbamate, thioether, bridged phosphoramidate, bridged methylene phosphate, bridged phosphorothioate and sulfone internucleotide linkages.

3. The oligonucleotide according to claim 2, wherein the oligonucleotide is a chimeric oligonucleotide comprising a phosphorothioate, phosphodiester or phosphorodithioate region and an alkylphosphonate or alkylphosphonothioate region.

4. The oligonucleotide according to claim 3, wherein the oligonucleotide comprises a ribonucleotide or 2'-O-substituted ribonucleotide region and a deoxyribonucleotide region.

5. A method for inhibiting tumor growth in a mammal, including a human, comprising administering to the mammal, which has at least one tumor cell present in its body, an antisense oligonucleotide according to claim 1 under conditions where tumor growth is inhibited.

6. An oligonuclcotide having from 21 to 35 nucleotides, which inhibits DNA methyltransferase expression, and comprises a nucleotide sequence selected from the group consisting of Sequences set forth in the Sequence Listings as SEQ ID NO 39, SEQ ID NO 40, SEQ ID NO 41, SEQ ID NO 42, SEQ ID NO 43, SEQ ID NO 44, SEQ ID NO 45, SEQ ID NO 46, SEQ ID NO 47, SEQ ID NO 48, SEQ ID NO 49, SEQ ID NO 50, SEQ ID NO 51, SEQ ID NO 52, SEQ ID NO 53, SEQ ID NO 54, SEQ ID NO 55, SEQ ID NO 56, SEQ ID NO 57, SEQ ID NO 58, SEQ ID NO 59, SEQ ID NO 60, SEQ ID NO 61, SEQ ID NO 62, SEQ ID NO 63, SEQ ID NO 64, SEQ ID NO 65, SEQ ID NO 66, SEQ ID NO 67, SEQ ID NO 68, SEQ ID NO 69, and SEQ ID NO 70.

7. A method for inhibiting tumor growth in a mammal, including a human, comprising administering to the mammal, which has at least one tumor cell present in its body, an antisense oligonucleotide according to claim 6 under conditions where tumor growth is inhibited.

8. An oligonucleotide having from 13 to 19 nucleotides, which inhibits DNA methyltransferase expression, and comprises a nucleotide sequence within a nucleotide sequence selected from the group consisting of Sequences set forth in the Sequence listings as SEQ ID NO 39, SEQ ID NO 40, SEQ ID NO 41, SEQ ID NO 42, SEQ ID NO 43, SEQ ID NO 44, SEQ ID NO 45, SEQ ID NO 46, SEQ ID NO 47, SEQ ID NO 48, SEQ ID NO 49, SEQ ID NO 50, SEQ ID NO 51, SEQ ID NO 52, SEQ ID NO 53, SEQ ID NO 54, SEQ ID NO 55, SEQ ID NO 56, SEQ ID NO 57, SEQ ID NO 58, SEQ ID NO 59, SEQ ID NO 60, SEQ ID NO 61, SEQ ID NO 62, SEQ ID NO 63, SEQ ID NO 64, SEQ ID NO 65, SEQ ID NO 66, SEQ ID NO 67, SEQ ID NO 68, SEQ ID NO 69, and SEQ ID NO 70.

* * * * *

UNITED STATES PATENT AND TRADEMARK OFFICE
CERTIFICATE OF CORRECTION

PATENT NO. : 6,221,849 B1
DATED : April 24, 2001
INVENTOR(S) : Moshe Szyf, Pascal Bigey and Shyam Ramchandani It is certified that error appears in the above-identified patent and that said Letters Patent is hereby corrected as shown below:

<u>Title page,</u>
Item [73], Assignee, should read as follows:
-- [73] Assignee: McGill University, Quebec, CANADA --.

Signed and Sealed this

Twentieth Day of August, 2002

*Attest:*

*Attesting Officer*

JAMES E. ROGAN
*Director of the United States Patent and Trademark Office*

SEQUENCE LISTING

<160> NUMBER OF SEQ ID NOS: 138

<210> SEQ ID NO 1
<211> LENGTH: 111
<212> TYPE: DNA
<213> ORGANISM: Homo sapiens

<400> SEQUENCE: 1

| | | | | | | |
|---|---|---|---|---|---|---|
| tcggggcagg | gtggcggggg | taggaggcag | cgccgagcgg | ctggctggaa | gagagtggtg | 60 |
| tgatggacgg | gcagcttcct | gtgtgctcca | agggatgagc | ctcgtcgggc | g | 111 |

<210> SEQ ID NO 2
<211> LENGTH: 4136
<212> TYPE: DNA
<213> ORGANISM: Homo sapiens

<400> SEQUENCE: 2

| | | | | | | |
|---|---|---|---|---|---|---|
| tttccccatg | ttttcttcta | ggagcactat | agtttcaggt | cttatgttta | atctttaata | 60 |
| agttttgtgt | ttttgtatat | ggtgtaaggt | aagggtccaa | cttcattctt | ttgtatgtgg | 120 |
| ttatacagtt | ttctcagcac | catttgttaa | agacacaatc | tttcccccat | gttctggtgc | 180 |
| tttaaaaaaa | aaaaaaatcc | tggctggtta | cggtggctta | ggcctataat | cccagcactt | 240 |
| tgggaggctg | aggcaagtgg | actgcttgag | gctaggagtc | ccagactagc | ctggccaaca | 300 |
| tggtgaaacc | ctgtctctac | caccgaagat | acaaaaatta | gccaggcgtg | gtggagtacg | 360 |
| cctgtaatcc | cagcctacta | gggaggctga | ggcatgagaa | tcgcttgaac | ctgggaggca | 420 |
| gaggttgcag | tgagccaaga | tctcaccact | gcacgccagc | cggggtgaca | gagtgaggca | 480 |
| gggtcttacc | ctgtcgccca | ggcaggagtc | cagtggccca | atcatggctc | attgcagcct | 540 |
| acactgccag | ggttcaagcc | atcctcccac | ctcagcctcc | caagtagcta | ggattacagg | 600 |
| tgtgtgtcac | catcccagca | aatcttgtat | ttttgtagag | atgggtatcc | ctatgttgct | 660 |
| caggctggtc | ttgaactcct | aacctcaagc | gatcctccca | cctgggcctc | tcaaagcact | 720 |
| gggtacaggc | gtgagccact | gcgcctgaca | tggtgcttct | taatttattc | ttactttta | 780 |
| tttttatttt | tttgagacaa | ggtcttgctc | tgtctcccag | gctggaatgt | agtggtacaa | 840 |
| tcatggctca | ctgcaacctc | tgcctctccg | gttcaagtga | tcttcctgcc | tcaacctctg | 900 |
| gagtagtttg | gactatgggc | acatgccaca | acgactagct | aatttttgtt | tttcttttt | 960 |
| tctttctttc | tttctttctt | tctttttttt | ttttttgag | atgcagtttc | tctatgttac | 1020 |
| ctaggctggt | ctaaaactcc | tgggctcaag | cgatcctccc | accctggcct | cccaaagtgc | 1080 |
| tgggatgaca | ggcgtgagcc | acgtggtgct | taaaaaaggc | aacaaaaaac | ccccacaca | 1140 |
| ctgggtatag | aagtggcatg | gggcctctat | acactgtgag | attcttggta | ctagctacaa | 1200 |
| attctgtgta | tactcaagat | tttctagagt | aggtggcaat | taccccgttt | tacagatgag | 1260 |
| gacacagagg | ctgagccgta | gtgacccacc | taaggtcgta | tagccagcaa | atagatggag | 1320 |
| gttggattgg | aaactgagga | ctttactcaa | gggctctcac | aacccttggg | gggcttctcg | 1380 |
| ctgctttatc | cccatcacac | ctgaaagaat | gaatgaatga | atgcctcggg | caccgtgccc | 1440 |
| acctcccagg | aaacgtggag | cttggacgag | cccactcgtc | cgcgtggggg | gggtgtgtgc | 1500 |
| ccgccttgcg | catgcgtgtt | ccctgggcat | ggcggctcc | gttccatcct | tctgcacagg | 1560 |
| gtatcgcctc | tctccgtttg | gtacatcccc | tcctccccca | cgcccggact | ggggtggtag | 1620 |
| acgcgcctcc | gctcatcgcc | cctccccatc | ggtttccgcg | cgaaaagccg | gggcgcctgc | 1680 |

```
gctgccgccg ccgcgtctgc tgaagcctcc gagatgccgg cgcgtaccgc cccagcccgg    1740
gtgcccacac tggccgtccc ggccatctcg ctgcccgacg atgtccgcag gcggtaggta    1800
ccatgggggg gaacacggac tcaggggac aggcagggcc ctgggtgggg ggtcgcttcc    1860
cctcggggtg gccggtggcg ctgctgacag acgggcgcgc atggctgggg tggtgcggcg    1920
cgcagcgcag ttggcgcggg cagggtggca cttccggtcg cgcgtgcccg ggctgtttgg    1980
cgccaaaatg gaccgtggat tcccccgtag ctccctggtg gctagaaact aggcggggtg    2040
ggcctctctt ttgatcccca aatacagctt tccccatgtt ttcttctagg agcactatag    2100
tttcaggtct tatgtttaat ctttaataag ttttgtgttt tgtatatgg tgtaaggtaa    2160 gggtccaact tcattctttt gtatgtggtt atacagtttt ctcagcacca tttgttaaag    2220
acacaatctt tccccatgt tctggtgctt taaaaaaaaa aaaatcctg gctggttacg    2280 gtggcttagg cctataatcc cagcactttg ggaggctgag gcaagtggac tgcttgaggc    2340
taggagtccc agactagcct ggccaacatg gtgaaaccct gtctctacca ccgaagatac    2400
aaaaattagc caggcgtggt ggagtacgcc tgtaatccca gcctactagg gaggctgagg    2460
catgagaatc gcttgaacct gggaggcaga ggttgcagtg agccaagatc tcaccactgc    2520
acgccagccg gggtgacaga gtgaggcagg tcttaccct gtcgcccagg caggagtcca    2580
gtggcccaat catggctcat tgcagcctac actgccaggg ttcaagccat cctcccacct    2640
cagcctccca gtagctagg attacaggtg tgtgtcacca tcccagcaaa tcttgtattt    2700
ttgtagagat gggtatccct atgttgctca ggctggtctt gaactcctaa cctcaagcga    2760
tcctcccacc tgggcctctc aaagcactgg gtacaggcgt gagccactgc gcctgacatg    2820
gtgcttctta atttattctt acttttatt tttattttt tgagacaagg tcttgctctg    2880
tctcccaggc tggaatgtag tggtacaatc atggctcact gcaacctctg cctctccggt    2940
tcaagtgatc ttcctgcctc aacctctgga gtagtttgga ctatgggcac atgccacaac    3000
gactagctaa ttttttgtttt tctttttttc tttctttctt tctttctttc ttttttttt    3060 tttttgagat gcagtttctc tatgttacct aggctggtct aaaactcctg gctcaagcg    3120 atcctcccac cctggcctcc caaagtgctg ggatgacagg cgtgagccac gtggtgctta    3180
aaaaaggcaa caaaaaccc cccacacact gggtatagaa gtggcatggg gcctctatac    3240
actgtgagat tcttggtact agctacaaat tctgtgtata ctcaagattt tctagagtag    3300
gtggcaatta ccccgtttta cagatgagga cacagaggct gagccgtagt gacccaccta    3360
aggtcgtata gccagcaaat agatggaggt tggattggaa actgaggact ttactcaagg    3420
gctctcacaa cccttggggg gcttctcgct gctttatccc catcacacct gaaagaatga    3480
atgaatgaat gcctcgggca ccgtgcccac ctcccaggaa acgtggagct tggacgagcc    3540
cactcgtccg cgtgggggg gtgtgtgccc gccttgcgca tgcgtgttcc ctgggcatgg    3600
ccggctccgt tccatccttc tgcacagggt atcgcctctc tccgtttggt acatcccctc    3660
ctcccccacg cccggactgg ggtggtagac gcgcctccgc tcatcgcccc tcccatcgg    3720 tttccgcgcg aaaagccggg gcgcctgcgc tgccgccgcc gcgtctgctg aagcctccga    3780
gatgccggcc cgtaccgccc cagcccggt gcccacactg gccgtcccgg ccatctcgct    3840
gcccgacgat gtccgcaggc ggtaggtacc atggggggga acacggactc aggggacag    3900 gcagggcgct gggtggggg tcgcttccc tcggggtggc cggtggcgct gctgacagac    3960
gggcgcgcat ggctggggtg gtgcggcgcg cagcgcagtt ggcgcgggca gggtggcact    4020
```

```
tccggtcgcg cgtgcccggg ctgtttggcg ccaaaatgga ccgtggattc ccccgtagct    4080
ccctggtggc tagaaactag gcggggtggg cctctctttt gatccccaaa tacagc        4136

<210> SEQ ID NO 3
<211> LENGTH: 87
<212> TYPE: DNA
<213> ORGANISM: Homo sapiens

<400> SEQUENCE: 3
aggaggtctt gcctcaaact tgccggctta aaggacatac atttattacc ttatgtccag      60
ggtcagaaat ctgatgcggg tttcacc                                         87

<210> SEQ ID NO 4
<211> LENGTH: 4460
<212> TYPE: DNA
<213> ORGANISM: Homo sapiens

<400> SEQUENCE: 4
tctagagctc gcggccgcga cgtcaattaa ccctcactaa agggagtcga ctcgatcgcc      60
ctatgttgtc cagggctgga ctcgaactcc tgcccacaag ccatcctccc accacagcct    120
cctgagtagc tggggttaca ggcacgcagc accgcggcac tgcaccggct tttgttcttt    180
tatttttttc cctctttgtc cctgaaagag tcaagctact aattgtcagt aatcaaatca    240
gaccacgatt tcccaggcaa actcctggca gttctacatt taggaatgac tagctagaga    300
catcctgaag aatgagttat tcggggaggc gccacgacct cctctaactt cacctctatc    360
tgccctctgt gtgggtaccc cttgcttccc tggatgcttg actcccccat ttcatcctca    420
aaatgccacc ccccccacc aggcctttag gaacatcagc tggctgttcc ccacagtgtc      480
ctgtggccct gggctactca ttctgacact ggccatactg tggcacacct tgttatgggc    540
tgttgtcaga cccaactgga gaagaccag ctgtaggtca tttcccttac gggagtgccc      600
caactatatg acctgccccc tctttcctgg tatcttttg agtcagggtc tcactctgtc      660
tcctagattg gagtgcagtg atgcaatcac ggctcactgt ggcctcgacc tcccaggctc    720
aggtgatctt cttctcagcc tcccaagtaa ctgggaccac aagcacatgc caccaaaccc    780
agttattttt attttatttt attttatttt attttgagac agagtttcac tcttgttgcc    840
caggctagag tgcaatggtg tgaccagctc actgcaacct ctgcctcccg ggttcaagtg    900
attctcctgc tcagcctcca agttgctggg attacagcca ccaccaccc acgcctggct      960 aattttttgta tttttagtag agatgggggtt tcgccatgtt ggccaggctg gtctcaaacc   1020
cttgacctca ggtaatccac ccaccttggc cctcaggtaa tccacccaac tgctgctgta    1080
tgttgggatt ccaggcatca gccaccacgc ccagccacta attttttgtat ttttgtagag    1140 atggagtttc gccatgtttc ccaggctggt ctgaacgcct gggctcaagt gatccgctcg    1200
ccttggcctc ccaaagagct gggattataa gcgtgagcca ccatgcctgg tctctggtac    1260
cttttaaaat atacaggctg gcatgatgg ctcatgcctg taatcccagc actttgggag      1320
gctgaggcag gtggatcgcc tgaggtcggg agttcgaaac ctagcctgac caacacggag    1380
aaaccctgtc tctgctaaaa atataaaatt agctgggtga tggtggtgca tgcctgtaat    1440
ccagctactc gggaggctga gccaggagaa tcgcttgaac ctgggagtcg gaggtttgag    1500
ctgagatcac accattgcac tccagcctgg gcaacaagag caaaaccta tctcaaaaaa      1560 aaaaaatata tatatatata tatatatata tacacagcta tatatagcgt atatatatat    1620
acacacacat atgtatacat atatacgtat gtatacacat atatacgtat atatacacat    1680
```

```
atatatgtat atatacacac atatacgtgt atatatatac gtgtatatat atatgcatgc   1740
cagacaaggt gactcatgcc tgtaatccta gcacttcagg agactgaggc aggcggattc   1800
acttgaggtc aggaatctaa gaccaggctt aaccaacatg gtgaaaccct gtctctactc   1860
aaaatacaaa aaattaacga ggctggtggc acctataatc ccagctactt gggagggctg   1920
aggtgagaga atcacttgaa cccagaaggt gagggttgca gtgagctgag atcgcaccac   1980
tgcactccac ctgggcaaca gagcgagact ccatgtctgt ctgtctgtct atctatctgt   2040
ataatgtata tgtatgtatg tatatatgtg tgtgtatata tatacacata tatacataca   2100
tatatacaca catactctgt tacagagctg ctgtgtgtgt gtgtatatat atatacacat   2160
atgtatatat acacatatac acatatatat gtatatatat acacacatat atatacacat   2220
atatatgtat atatatacac acatatatat acacatatat atgatatata tacacatata   2280
tatgtatata tatacacaca cacacacata cacataattg tgttacagag ctgctatgta   2340
atctcacaat catcagaaaa atgaccccca aaggggaaac cttgttcaga tcagatgact   2400
tcttagcatt aggcattcca gtaggacact ctagactctt gcggggagac aaaagccagc   2460
ttagtttttt ctaacactca tatgttaaac ttgtttgtgt ccaaaacttc tttagaactg   2520
tgatattctt acaggcaaat gaagttgctt aacaagtgtt gtatttttct ccctatttct   2580
tcctccaggc tcaaagattt ggaaagagac agcttaacag aaaaggtaat ctcctcctta   2640
aaatttttct tattaccaaa tctgactgac acactttgtg gctcataaaa agaaatttgt   2700 tttcttaaa tggattttgc attttttccc atggagtttc aaagataatt tggatattct   2760
tgttaaatgt cagcactaat ttgctgctaa tagttgggtg gtggtggtgt tttttttgt   2820 tgttgttttt gtttttgag acagagtctc actctgtcac ccaggctaga gtgcaatggc   2880
atgatctcgg cctcactgtg acctctgcct cccggattca gctgttctc ctgcctcagc   2940 ctcccaagta gctgggacta caggcacgca ccaccatgcc cagctaattt ttatattatt   3000
agtagagatg gggtttacca tgttggccag actggtcttg aacgcctgct cgtgatctgc   3060
ccaccttggc ctcccaaagt gctggaatta caggcgtgac gaccatgcct ggcccaggtt   3120
tttttttttt ttaaccaatc tcagttccta aacaactcta ctctggattg taacttgtcc   3180
tggtaacact gttttattgt gttttttgtta ttgttttgag atagggctct cattctgtag   3240
cccaggctgg agtgcagtgg cacaattttg gctcactgca accttcgcct cccaggctca   3300
agtgattttc ccactcagcc tcctgagtag ctctaactac aggctcaagc caccatgccc   3360
agctaatttt taaatatttt ttgtaaagat gggattttgt catgttgccc caggctggtc   3420
ttgaactctg gggctcaaag caatccactt gcctcggcct cccaaagtgc tgggattata   3480
ggtgtgagcc actgtgcctg gccgacact ttacagaagc acagtattat tcttataaac   3540
catgatatgt ctccatctca cctccagctt tcccattttt caccactttg gagacaggag   3600
tgaagtgatc ctaatggaaa ttccctgaac acatttcatg actgtttagt gttttgactg   3660
agacagcatt gcctgccatt cactcattgt gatgtgatca ggcagctcaa taatttgtgt   3720
attagtccac tagtgaatag cttgggaatg tgggtactgc taaacctata tccttccctt   3780
aggaatgtgt gaaggagaaa ttgaatctct tgcacgaatt tctgcaaaca gaataaaga   3840 atcagttatg tgacttggaa accaaattac gtaaagaaga attatccgag gtaagtcagt   3900
tctcagcatc ctagcctcta gaaaaatgtc tcctcctagt aacttgtctg tgaccaggga   3960
ggcagcaaga tccccagctg tcctcattgc ctgatgatga tgatgatgat gatgatgatg   4020
```

-continued

```
aagaacacat gtgttctgtc tctgacacgt gttacattca ctgctactaa ttatcctgtc    4080
ctgctgtagg agggctacct ggctaaagtc aaatccctgt taataaagat tttgtccttg    4140
agaacggtgc tcatgcttac aaccggaagt gaatggacgc tagaaaacg ggaaccaagc     4200 aagaagtgaa gcccgtagag tgggaatggc agatgccaac agccccccca aaccccttc     4260 caaacctcgc acgcccagga ggagcaagtc cgatggagag gctaagcgta agagcagatg    4320
attcctttta tttttaattg tttttgagat ggagtctcac tgtgttgccc agtctggagc    4380
acagtggtgt aacctcggct cactgtaacc tctgcctcca ggttcaagag accctcctgc    4440
ctcagcctcc caagtaactg                                                4460
```

<210> SEQ ID NO 5
<211> LENGTH: 348
<212> TYPE: DNA
<213> ORGANISM: Homo sapiens

<400> SEQUENCE: 5

```
gccaacatta gcaagctggt tgttgactag aataaaaatg caaagatgct agtccttaga     60
acctgggctt cctgcaatag cttagtaatg ttgaactgca ttattgctgt gggctttcta   120
ttgatagtgg ctttttttttt tcttttttaat gcttttctct ctttaaacag ctgaaccttc   180
acctagcccc aggattacaa ggaaaagcac caggcaaacc accatcacat ctcattttgc   240 aaagggtca gtatacgata aattggcggc tgccttttt aggggccggc tgttttggga    300
tggaattggt agggcgtcac gtggcaattc tgtcttccgt gttgtata                348
```

<210> SEQ ID NO 6
<211> LENGTH: 454
<212> TYPE: DNA
<213> ORGANISM: Homo sapiens

<400> SEQUENCE: 6

```
tctctgacac tagcagctgt tgatcggtgt ttagacccgt gatttcttag gacttacaag     60
atggcaagac aacattctaa acccgtcatt cagagaaaca ttaaacttga agcctctttc    120
aacatcctgg tgaatgaggg tccacttcag gccagctgga ggcctagggt cttgttccac    180
taatggttgg cctcactgtg tgtgacagcc ctgccaaacg gaaacctcag gaagagtctg    240
aaagagccaa atcggatgag tccatcaagg aagaagacaa agaccaggta gggccagtgc    300
tttcatttcc tgactctacc ttacttggtg tatttgatga ttgtgacttc atatgtgttc    360
tgtccaagta aataaaaacc ctgtctaggg ctctatttag ggctctccag agagacagga    420
ccaatagaat gtatatgtgt gtatcaacgt atag                                454
```

<210> SEQ ID NO 7
<211> LENGTH: 305
<212> TYPE: DNA
<213> ORGANISM: Homo sapiens

<400> SEQUENCE: 7

```
gttttggggt tggtggggat taataccaga gtaagagttt ctcagatctt ctccccttttt    60 cccaggcccc ttcttttccc actcttgctc taaccatgtc aaatgtgtta atatttcaac    120
tcacactttt ggtgttgacc ttcccttgaa accagtattc taatcttttt tgttcttcct   180
tccctccaca caggatgaga agagacgtag agttacatcc agagaacggt aagaatagtt    240 actataccctt tcttttttgtt ctacgagttg tgtaatcttg atcacaaaac tttttcagaa   300
agttt                                                                305
```

<210> SEQ ID NO 8
<211> LENGTH: 223
<212> TYPE: DNA
<213> ORGANISM: Homo sapiens

<400> SEQUENCE: 8
cagggctccg agataagtaa gattgctttt ggggaaaaga ggagctttat gaaaactgct      60
tctttgggga agctcctggc actcacactt ggggtctgtg ttattttgct tgacagagtt     120
gctagaccgc ttcctgcaga agaacctgaa agagcaaaat caggaacgcg cactgaaaag     180
gaagaagaaa gagatgaaaa agtaaagctc tatcacctct aag                       223

<210> SEQ ID NO 9
<211> LENGTH: 396
<212> TYPE: DNA
<213> ORGANISM: Homo sapiens

<400> SEQUENCE: 9
tacaggcgtg agctactgtg cccactggta gacagtcttt actcccacca gtgactctag      60
aatcagttca ggtgttttat ttccatagga cactttaata gaaagatcca accaaatgg      120 aaaaaattaa cttgtctttt ttccctgcaa cttaggaaga aaagagactc cgaagtcaaa     180
ccaaagaacc gtaagtgcag cgaacctgcc tttgtgcttt gttgtgaaac tgaattgcta     240
acataagtat cttggtaaaa taacgggttg gtgtggaaca gtgggcgcta atcatatgtc     300
tcttatgtgg gcaagttctg cttgtgaaag gtgagaccac cctgaagtga aggctgaagt     360 taacttttt aactttaatt taatttaatt taattt                                396

<210> SEQ ID NO 10
<211> LENGTH: 43
<212> TYPE: DNA
<213> ORGANISM: Homo sapiens

<400> SEQUENCE: 10
cttcagtttc tgtttgggtg ttggttcttt ggtttgactt cgg                        43

<210> SEQ ID NO 11
<211> LENGTH: 254
<212> TYPE: DNA
<213> ORGANISM: Homo sapiens

<400> SEQUENCE: 11
tgagtcctga gtagtaaatc gtctggcttc ctgcagtgaa gacaggagag gcagcctgtc      60
ctctgaacct ggggaggagc ttgtgtcagc ccttaggagc tgttggcccc ggtgcagggc     120 ccccccgag ctgaccagcc tgtgtgtgtg ttgtcttctg tgacagaaca cccaaacaga     180
aactgaagga ggagccggac agagaagcca gggcaggcgt gcaggctgac gaggacgaag     240
atggagacga gaaa                                                       254

<210> SEQ ID NO 12
<211> LENGTH: 281
<212> TYPE: DNA
<213> ORGANISM: Homo sapiens

<400> SEQUENCE: 12
agaaactaat ttttcccctt ctttatctct ctacctcccc cttatttttc tgtcaggatg      60
agaagaagca cagaagtcaa cccaaagatc tgcaagtgtt taaaatgctt gtgcttttgt     120

| | |
|---|---|
| gtcatctgga tcagtagaaa gcctgttcta ggccaaggtg tggtggcttg cacctgtaat | 180 |
| cccagctcaa agggaggctg aggtgggtga atcacctgag gtcaggagtt cgagaccagc | 240 |
| ctagcctggc caacatggtg gaaccctgtc tgtactaaaa a | 281 |

<210> SEQ ID NO 13
<211> LENGTH: 249
<212> TYPE: DNA
<213> ORGANISM: Homo sapiens

<400> SEQUENCE: 13

| | |
|---|---|
| atcttggctt tcccatgggg aggcattagt ttgtcacttt ccgtgcgagt tggcgatgtg | 60 |
| gttagtgttt ctaagcttgc tacttgctgt gtatctgttc accctgcaga gctgccaaac | 120 |
| ggaggcccga agaaaaagaa cctgaaaaag taaatccaca gatttctgat gaaaaagacg | 180 |
| aggatgaaaa ggtaaaggtc tcacttttct ttctttcttt tttttttttt tttttttcccc | 240 |
| aagacgggg | 249 |

<210> SEQ ID NO 14
<211> LENGTH: 291
<212> TYPE: DNA
<213> ORGANISM: Homo sapiens

<400> SEQUENCE: 14

| | |
|---|---|
| gactataaga tttgtattct atgactttag atggtagagt gagtcagagc tcacctgctg | 60 |
| gccctctcac tgcctccctc cccttctctc tgttttatga taatcactta tacaaagttc | 120 |
| ttaacaccga agcactatct gggaggaaaa cactctctta gcctttaatc ctcttttgtt | 180 |
| ttccctgtgt aggagaagag acgcaaaacg accccccaaag aaccgtaaga atttattctt | 240 |
| gacattatcc aaagcagatg gtaatgttaa aatgatggtt ctagaacaaa a | 291 |

<210> SEQ ID NO 15
<211> LENGTH: 491
<212> TYPE: DNA
<213> ORGANISM: Homo sapiens

<400> SEQUENCE: 15

| | |
|---|---|
| caacgatctt gtgattttt tttccccccag aacggagaaa aaaatggctc gcgccaaaac | 60 |
| agtcatgaac tccaaggtaa acatctgccg ggaataaagc cggtggcggc gctcacgagc | 120 |
| ggctgggagc tgctctctga gtgccatcat ctgtgttcct gctcccacag acccacccctc | 180 |
| ccaagtgcat tcagtgcggg cagtacctgg acgaccctga cctcaaatat gggcagcacc | 240 |
| caccagacgc ggttcgtaca gctctcttcc cagccttcct ctgcctgtcc cttgtcccac | 300 |
| tgctcaccag ccccgtgtcc ttcaggtgga tgagccacag atgctgacaa atgagaagct | 360 |
| gtccatcttt gatgccaacg agtctggctt tgagagttat gaggcgcttc cccagcacaa | 420 |
| actgacctgc ttcaggtaag tgcacttttcg tgtgcatgtt tgcttcgtgg aaggaggcac | 480 |
| atccccagag g | 491 |

<210> SEQ ID NO 16
<211> LENGTH: 1243
<212> TYPE: DNA
<213> ORGANISM: Homo sapiens

<400> SEQUENCE: 16

| | |
|---|---|
| ccatcctaat acgactcact atagggctcg agcggccgcc gggaggtctc tctgtcttca | 60 |
| ctaaagaacg tgctcccgaa tgtcaagggg catctggaca gtggccgcag tgtttgagat | 120 |

-continued

```
ttatgcccaa aaggaggcag aagtccttcc ttcccacatc cctttttcaca ctgttctata    180
acctgcttta ttttctaaat tgaggtctaa ctcgtataat ataaaattaa ccatatgagg    240
tatcttgaat aggtgaattc ataggtatag aaagcagatt ggtggttgcc gggggtgggg    300
gctgagggcc ggttgggagg agactggaga gtgactgcta cttgatggga atgaggcttt    360
attaacattt gagtgacaga aatgttctgc agctgaatag agctagtggc tgcactgcat    420
agtagaaggt gttctagaaa ccggtatttc ccgcactgta agtctgactg atctttttggt    480
gttgctgttg cagacacaca tacacttgat gcttaggtgg gagaataagg tagaaactct    540
gggtgataga acgctgtctt aatccagtgt tcccgcaacc aaaaaatgag tgtcggggcc    600
aggcatggtg gttcagcctg taatcccagc actttgggag gctgaggtgg gtagatcact    660
ggagataaag agtttgagac cagcctgcta cacatagtga aaccccgtcc ctactaaaaa    720
tacaacaatt agccgggcat ggtggttcag gcctgtaatc ccagctactc gggaggctga    780
ggcaggagaa ttacttgaac ccgggaggtg gaggctgcag tgagccaaga ttatgccatc    840
gcgctccagc ctgagggata gagcaagact ctgtctcaaa aacaaacaaa aaaagagtgt    900
cagacttgta cattctctca tttcctcgtg cctgatatga agtctgcacg aagaccccctt    960
cacggcttag ctggtaagca tgtgctttgt ttcctgtcta gtgtgtactg taagcacggt   1020
cacctgtgtc ccatcgacac cggcctcatc gagaagaata tcgaactctt cttttctggt   1080
tcagcaaaac caatctatga tgatgacccg tctcttgaag gtaaggaata gtccgggatt   1140
atgtttgggg cacactttaa aaacagccag gcaggttggc tcacatctgt aatcctagca   1200
ctttgggggc tgaggccaga ggatcacttg agcccgggag ttt                     1243
```

<210> SEQ ID NO 17
<211> LENGTH: 293
<212> TYPE: DNA
<213> ORGANISM: Homo sapiens

<400> SEQUENCE: 17

```
tttagtccat ttccttttc tgctctaggt ggtgttaatg gcaaaaatct tggccccata      60
aatgaatggt ggatcactgg ctttgatgga ggtgaaaagg ccctcatcgg cttcagcacc    120
tgtaagtgtg tggcccatca taggctggcc ggggtctgaa aggggccttc atgttctcct    180
tcctgggggc tgacgggget ctggtgggaa ttctcagcag gcttgcagaa ggccatgtga    240
ctgggaacct tagcaggttc agttgggta gatctcttgt gttagttagt agg            293
```

<210> SEQ ID NO 18
<211> LENGTH: 1094
<212> TYPE: DNA
<213> ORGANISM: Homo sapiens

<400> SEQUENCE: 18

```
cgctctctgg ctggctcaga caggcttctt cagaacaagc cagctatgat gtgttgtgcc     60
ctatgtttct gacatttggg tacgggatga cttttagact gttgggtgag tttggtagac    120
tcctccatgc cctgtggcca ctgtaggcgc catcagattc cagccccttt tccacacctc    180
ctctgttcgc cccagcattt gccgaataca ttctgatgga tcccagtccc gagtatgcgc    240
ccatatttgg gctgatgcag gagaagatct acatcagcaa gattgtggtg gagttcctgc    300
agagcaattc cgactcgacc tatgaggacc tgatcaacaa gatcgaggta agagatcgag    360
ggtcctcagc atccgggatt cccactggaa acttgccttc agaaccagca gacactgttc    420
```

| | |
|---|---|
| ttcagttgga tttaggccag tttggcttaa gcatgagaga aacctgttct ctttcaagac | 480 |
| cacggttcct ccttctggcc tcaacttgaa ccgcttcaca gaggactccc tcctgcgaca | 540 |
| cgcgcagttt gtggtggagc aggtggagag ttatgacgag gccggggaca gtgatgagca | 600 |
| gcccatcttc ctgacgccct gcatgcggga cctgatcaag ctggctgggg tcacgctggg | 660 |
| acagaggtaa ggatgcggct gggaccagag tgaagactgg agaccgggga gggtagagca | 720 |
| tggcccacat cctctgtccc agtcctctga gatgctggaa cctctcccgt aggcgagccc | 780 |
| aggcgaggcg gcagaccatc aggcattcta ccagggagaa ggacagggga cccacgaaag | 840 |
| ccaccaccac caagctggtc taccagatct tcgatacttt cttcgcagag caaattgaaa | 900 |
| aggatgacag agaagacaag gagaacgcct ttaagcgccg gcgatgtggc gtctgtgagg | 960 |
| taacctcacc tgtgggtgct cccgctcccc taaggtggcc cagcctctgg cctgatctga | 1020 |
| ggactgctcc atctttctct gtggcttgag actctggctg ctcaaatgtg accctgagac | 1080 |
| agaaattgtt gtgg | 1094 |

<210> SEQ ID NO 19
<211> LENGTH: 242
<212> TYPE: DNA
<213> ORGANISM: Homo sapiens

<400> SEQUENCE: 19

| | |
|---|---|
| ctgtgcccag cctgtttgcc tttttatgcc ttttttaggt gtgtcagcag cctgagtgtg | 60 |
| ggaaatgtaa agcctgcaag gacatggtta aatttggtgg cagtggacgg agcaagcagg | 120 |
| cttgccaaga gcggaggtag gtcaggccga gtcttcctcc tgtggcagag gacttgccag | 180 |
| ctggtggcag atgcactgtg gagaagggcc gtcatgtgtg ggacagcacc aggattcctt | 240 |
| cg | 242 |

<210> SEQ ID NO 20
<211> LENGTH: 83
<212> TYPE: DNA
<213> ORGANISM: Homo sapiens

<400> SEQUENCE: 20

| | |
|---|---|
| agacctgtcc ctgttatgaa gaaaacagcc ccggttggtc ttacttagaa aagggccctt | 60 |
| aggtataacc agtgacattg cag | 83 |

<210> SEQ ID NO 21
<211> LENGTH: 185
<212> TYPE: DNA
<213> ORGANISM: Homo sapiens

<400> SEQUENCE: 21

| | |
|---|---|
| gtgtcccaat atggccatga aggaggcaga tgacgatgag gaagtcgatg ataacatccc | 60 |
| agagatgccg tcacccaaaa aaatgcacca ggggaagaag aagaaacaga acaagaatcg | 120 |
| catctcttgg gtcggagaag ccgtcaaggt aaccctggga gtcccttgg ttcagtcctc | 180 |
| actgc | 185 |

<210> SEQ ID NO 22
<211> LENGTH: 61
<212> TYPE: DNA
<213> ORGANISM: Homo sapiens

<400> SEQUENCE: 22

| | |
|---|---|
| aagtcaaggc cagcaaagac cctcagaatg atcctccatg aacttatgct ctcattttca | 60 |

| | |
|---|---:|
| g | 61 |

<210> SEQ ID NO 23
<211> LENGTH: 180
<212> TYPE: DNA
<213> ORGANISM: Homo sapiens

<400> SEQUENCE: 23

| | |
|---|---:|
| actgatggga agaagagtta ctataagaag gtgtgcattg atgcggaaac cctggaagtg | 60 |
| ggggactgtg tctctgttat tccagatgat tcctcaaaac cgctgtatct agcaaggttt | 120 |
| gcatctttct ttttgcttga cttctgcatg cactttctca tcaagtagga gatgccctgt | 180 |

<210> SEQ ID NO 24
<211> LENGTH: 258
<212> TYPE: DNA
<213> ORGANISM: Homo sapiens

<400> SEQUENCE: 24

| | |
|---|---:|
| ctccccatgc ccgtcttcta ttccagggtc acggcgctgt gggaggacag cagcaacggg | 60 |
| cagatgtttc acgcccactg gttctgcgct gggacagaca cagtcctcgg ggccacgtcg | 120 |
| gaccctctgg agctgttctt ggtggatgaa tgtgaggaca tgcagctttc atatatccac | 180 |
| agcaaagtga aagtcatcta caaagccccc tccgaaaact gggccatgga ggtgagtgcc | 240 |
| tggtgtcctc gtgagccc | 258 |

<210> SEQ ID NO 25
<211> LENGTH: 241
<212> TYPE: DNA
<213> ORGANISM: Homo sapiens

<400> SEQUENCE: 25

| | |
|---|---:|
| gacccaaccg acgatatctt tgagtctccc aagggaggca tggatcccga gtccctgctg | 60 |
| gaggggacg acgggaagac ctacttctac cagctgtggt atgatcaaga ctacgcgaga | 120 |
| ttcgagtccc ctccaaaaac ccagccaaca gaggacaaca agttcaagtg agcactgggg | 180 |
| ctggactcgg ggtcagcagg cactttcagc ccacatcact ccctttttccc gtgtgcttcc | 240 |
| g | 241 |

<210> SEQ ID NO 26
<211> LENGTH: 282
<212> TYPE: DNA
<213> ORGANISM: Homo sapiens

<400> SEQUENCE: 26

| | |
|---|---:|
| aagctggcag tagctgctgc ggccactgcc ggccacctca gggccttatg tttctgtccc | 60 |
| tttgtttcct tcagattctg tgtgagctgt gcccgtctgg ctgagatgag gcaaaaagaa | 120 |
| atccccaggg tcctggagca gctcgaggac ctggatagcc gggtcctcta ctactcagcc | 180 |
| accaagaacg gcatcctgta ccgagttggt gatggtgtgt acctgccccc tgaggccttc | 240 |
| acgttcaagt aagtgccccc tcggagcagc cggggccagg gg | 282 |

<210> SEQ ID NO 27
<211> LENGTH: 433
<212> TYPE: DNA
<213> ORGANISM: Homo sapiens

<400> SEQUENCE: 27

```
aaatcatttc ttagggtaca cacctacctt aattcatcag gtgcttgact ttaaatggtt      60
attttcactg gtcagtcatg cctgactgac cactgcaagg tggaaggttc attgatgtca     120
agtgggtgct tctctgcagc atcaagctgt ccagtcccgt gaaacgccca cggaaggagc     180
ccgtggatga ggacctgtac ccagagcact accggaaata ctccgactac atcaaaggca     240
gcaacctgga tgcccctgag ccctaccgaa ttggccggat caaagagatc ttctgtccca     300
agaagagcaa cggcaggccc aatgagactg acatcaaaat ccgggtcaac aagttctaca     360
ggtcagcaga ggcctctgtt cttcctcgag gccacagact cttctagaag gctctgctga     420
aacaaggttg tgg                                                         433
```

<210> SEQ ID NO 28
<211> LENGTH: 394
<212> TYPE: DNA
<213> ORGANISM: Homo sapiens

<400> SEQUENCE: 28

```
aaaaggagag ctcctaacga ggcctactcc cgctcgcagg cctgagaaca cccacaagtc      60
cactccagcg agctaccacg cagacatcaa cctgctctac tggagcgacg aggaggccgt     120
ggtggacttc aaggctgtgc agggccgctg caccgtggag tatggggagg acctgcccga     180
gtgcgtccag gtgtactcca tgggcggccc caaccgcttc tacttcctcg aggtggtgcc     240
cctgcttgct agagggaagg cttcggggtc aaagttggcc agaaggagtc tgatgtcggg     300
ttatacacaa ggcggcttgg ctgcagggtt tcagcttttg taagaagtgg gtggttggct     360
gacgtgaagc tgttctgcag gagctttacg gggg                                  394
```

<210> SEQ ID NO 29
<211> LENGTH: 671
<212> TYPE: DNA
<213> ORGANISM: Homo sapiens

<400> SEQUENCE: 29

```
gtcaactact ctattggtgg ctaattggtc atggccccac tgaggagaat taagtgacta      60
tcaattgcct tcttactagt ctgcgttaga gaggggacag tggcgtttct ctcccaaacg     120
attgcagttc tctccttttc aggcctataa tgcaaagagc aaaagctttg aagatcctcc     180
caaccatgcc cgtagccctg gaaacaaagg gaagggcaag ggaaaaggta cgtcattgta     240
tgagtttctt ttcaagttat tcttctgtaa cttggaggct gcctgtgaat ccctcagtgt     300
aaaaccacct ctggtgttac tgactctggg acagcgaggc cgcctgagtt aacaaggcgc     360
ttgagagcaa ggtggacttg gactctgagg atcgggttta gcctctggcc tctctccccc     420
agggaagggc aagcccaagt cccaagcctg tgagccgagc gagccagaga tagagatcaa     480
gctgcccaag ctgcggaccc tggatgtgtt ttctggctgc gggggggttgt cggagggatt     540 ccaccaagca ggtgagcgcc cgtaggctcc atctctgaat acctggtgag cccagaccgg     600
gcaggtgcta cctgaaacga cttccaaccc ggtcaccttc tgatctaaga atctcttcga     660
ggccaggcac g                                                           671
```

<210> SEQ ID NO 30
<211> LENGTH: 452
<212> TYPE: DNA
<213> ORGANISM: Homo sapiens

<400> SEQUENCE: 30

```
actgcacgcc agcctgggtg acagagcgag actccatctc aaaaaaaaaa aaaaaatctt      60
```

```
ctggagagtt gaaagcatgg cttcgtgctt gatctgccag gcatctctga cacgctgtgg      120
gccatcgaga tgtgggaccc tgcggcccag gcgttccggc tgaacaaccc cggctccaca      180
gtgttcacag aggactgcaa catcctgctg aagctggtca tggctgggga gaccaccaac      240
tcccgcggcc agcggctgcc ccagaaggga gacgtggaga tgctgtgcgg cgggccgccc      300
tgccagggct tcagcggcat gaaccgcttc aattcgcgca cctactccaa gttcaaaaac      360
tctctggtgg tttccttcct caggtaaacg ggtagaagcc ccccagtgtt gccagacggc      420
ccggggctgt gcgcatgtca gcagtgtcat tt                                    452

<210> SEQ ID NO 31
<211> LENGTH: 434
<212> TYPE: DNA
<213> ORGANISM: Homo sapiens

<400> SEQUENCE: 31
gaagctcaca gctcagctct caccagggag agactttgat aacattcgtg aggggcttcc      60
ggcacagtgg gcgtttcttc cctctgtctg tggaggtgac tcctgcagtc tctcctgccc      120
cctacagcag ctactgcgac tactaccggc cccggttctt cctcctggag aatgtcagga      180
actttgtctc cttcaagcgc tccatggtcc tgaagctcac cctccgctgc ctggtccgca      240
tgggctatca gtgcaccttc ggcgtgctgc aggtgggccc tggggctggg gcgggcagac      300
agatgaggcc agcacgtgac ccggccagca gccagccatc ccttactgaa ggcagggttc      360
aatggcatag gcctgccatc caggcagcag aggctggcat ggtgctctgt ccactggcgg      420 atgagggag atcg                                                         434

<210> SEQ ID NO 32
<211> LENGTH: 317
<212> TYPE: DNA
<213> ORGANISM: Homo sapiens

<400> SEQUENCE: 32
cgactcagct gctgaccctg ggcctgggtc tggccagtcc agttgggagt gtcccactga      60 cggtgggtt gtccgtcctt ctcccccaca ggccggtcag tacggcgtgg cccagactag       120
gaggcgggcc atcatcctgg ccgcggcccc tgagagaaag ctccctctgt tcccggagcc      180
actgcacgtg tttgctcccc gggcctgcca gctgagcgtg gtggtggatg acaagaagtt      240
tgtgagcaac ataaccaggt aggtggcccc cgtcgctcct ccacacactg ccgacgaggc      300
ctcagtagct catgggg                                                     317

<210> SEQ ID NO 33
<211> LENGTH: 489
<212> TYPE: DNA
<213> ORGANISM: Homo sapiens

<400> SEQUENCE: 33
catagcccca tcccccttc cagatggcat ccagcacact gccacccatg tgacctcggg        60
cagtgctgtg atctcgggag aaggccatct gagcaggcag ggggtggcac ctgtgatgag      120
gggacagctg ctgcgtgcat ctccagaggt gttgacctcc tcctgtgttg caggttgagc      180
tcgggtcctt tccggaccat cacggtgcga gacacgatgt ccgacctgcc ggaggtgcgg      240
aatggagcct cggcactgga gatctcctac aacgggagc ctcagtcctg gttccagagg       300
cagctccggg gcgcacagta ccagcccatc ctcagggacc acatctgtaa ggtaatggca      360
```

-continued

| ccctgacaga gcggctcctc ctcgaggccc agcccagcag cctcgtggga acagtcagcc | 420 |
| tgcccaagac tcaggggaga catggaatct gatcccaggc tcctcctccg agtctcagcc | 480 |
| tttgtgtga | 489 |

<210> SEQ ID NO 34
<211> LENGTH: 285
<212> TYPE: DNA
<213> ORGANISM: Homo sapiens

<400> SEQUENCE: 34

| atggacacgt cccccacac tctttcagga catgagtgca ttggtggctg cccgcatgcg | 60 |
| gcacatcccc ttggcccag gtcagactg gcgcgatctg cccaacatcg aggtgcggct | 120 |
| ctcagacggc accatggcca ggaagctgcg gtatacccac catgacagga agaacggccg | 180 |
| cagcagctct ggggccctcc gtgggtctg ctcctgcgtg aaggtgggt cctgtaagtt | 240 |
| gtggttcccg gtggctgagg ggaaggaagg cagacctggg cctttt | 285 |

<210> SEQ ID NO 35
<211> LENGTH: 382
<212> TYPE: DNA
<213> ORGANISM: Homo sapiens

<400> SEQUENCE: 35

| gacagagtgc catctctgcc tcccaaagct ctaagagcca tgtcccaagc ctatacccca | 60 |
| tcccacaact gcagcctcat cactgtcctg tcttccagcc ggcaaagcct gcgacccgc | 120 |
| agccaggcag ttcaacaccc tcatcccctg gtgcctgccc cacaccggga accggcacaa | 180 |
| ccactgggct ggcctctatg gaaggctcga gtgggacggt tcttcagca caaccgtcac | 240 |
| caaccccgag cccatgggca agcaggtagg tggggagggg gcatccgagg gcctgggtca | 300 |
| ggctgtactt ggcggcctaa ctaggtggaa gtgtgggttt agccaagtgg gggacagcac | 360 |
| cccaggatcc cccaggcacc tg | 382 |

<210> SEQ ID NO 36
<211> LENGTH: 353
<212> TYPE: DNA
<213> ORGANISM: Homo sapiens

<400> SEQUENCE: 36

| agactgctct gcctcctgcc cctccacgtc cacggacaag ctcatagcca agccatggcc | 60 |
| gtatgctgtc acagtgccat ttccctccct gtccccgacg gtgacccggc ctgggtgcta | 120 |
| ctgccctcgc ccaccgcgcc tctttccccc agggccgcgt gctccaccca gagcagcacc | 180 |
| gtgtggtgag cgtgcgggag tgtgcccgct cccagggctt ccctgacacc taccggctct | 240 |
| tcggcaacat cctggacaag caccggcagg tcagtggggc ggcgcgctgg gtctggacag | 300 |
| gaaggaggct tctgtgcctg tcaccaggtg gggctggggc agcgcagtca ctt | 353 |

<210> SEQ ID NO 37
<211> LENGTH: 254
<212> TYPE: DNA
<213> ORGANISM: Homo sapiens

<400> SEQUENCE: 37

| caatgcccag gttgtcctcc atctgagcag gtgctggagt acacctcccc cggccttggg | 60 |
| cctggtgtcc acatcaggca ttgcccttct cccctcctgc aggtgggcaa tgccgtgcca | 120 |
| ccgcccctgg ccaaagccat tggcttggag atcaagcttt gtatgttggc caaagcccga | 180 |

```
gagagtgccg tatggtgggg tgggccaggc ttcctctggg gcctgactgc cctctggggt      240
acatgtgggg gcag                                                        254
```

<210> SEQ ID NO 38
<211> LENGTH: 565
<212> TYPE: DNA
<213> ORGANISM: Homo sapiens

<400> SEQUENCE: 38

```
actgagcctc tgggtctaga acctctgggg accgtttgag gagtgttcag tctccgtgaa       60
cgttccctta gcactctgcc acttattggg tcagctgtta acatcagtac gttaatgttt      120
cctgatggtc catgtctgtt actcgcctgt caagaggcgt gacaccgggc gtgttcccca      180
gagtgacttt tcctttattt tcccttcagc taaaataaag gaggaggaag ctgctaagga      240
ctagttctgc cctcccgtca ccctgtttc tggcaccagg aatccccaac atgcactgat       300
gttgtgtttt taacatgtca atctgtccgt tcacatgtgt ggtacatggt gtttgtggcc      360
ttggctgaca tgaagctgtt gtgtgaggtt cgcttatcaa ctaatgattt agtgatcaaa      420
ttgtgcagta ctttgtgcat tctggattt aaaagttttt tattatgcat tatatcaaat      480
ctaccactgt atgagtggaa attaagactt tatgtagttt ttatatgttg taatatttct      540
tcaaataaat ctctcctata aacca                                            565
```

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 39

```
agaactgact tacctcggat                                                   20
```

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence:  Synthetic
      Oligonucleotide

<400> SEQUENCE: 40

```
agggtgggtc tgtgggagca                                                   20
```

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 41

```
cagtacacac tagacaggaa                                                   20
```

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic Oligonucleotide

<400> SEQUENCE: 42
cacacttaca ggtgctgaag                                                20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 43
gatctcttac ctcgatcttg                                                20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 44
cgcatcctta cctctgtccc                                                20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 45
ggtgaggtta cctcacagac                                                20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 46
ggcctgacct acctccgctc                                                20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 47
ccaagggtta ccttgacggc                                                20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

```
<400> SEQUENCE: 48
aaagatgcaa accttgctag                                              20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 49
tccatgcctc ccttgggtag                                              20

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 50
ccagtgctca cttgaacttg                                              20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 51
acacagaatc tgaaggaaac                                              20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 52
agcttgatgc tgcagagaag                                              20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 53 cagggcacc acctcgagga                                               20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide
```

```
<400> SEQUENCE: 54
cttgcccttc cctgggggag                                              20

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 55
acggccgctc acctgcttgg                                              20

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 56
tcccggcctg tgggggagaa                                              20

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 57
gggccaccta cctggttatg                                              20

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 58
gggtgccatt accttacaga                                              20

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 59
acaggaccca ccttccacgc                                              20

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 60
```
gcacgcggcc ctgggggaaa                                              20

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 61
gccccactga ctgccggtgc                                              20

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 62
cccgggtggt atgccgtgag                                              20

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 63
ctgctcttac gcttagcctc                                              20

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 64
gaaggttcag ctgtttaaag                                              20

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 65
gtttggcagg gctgtcacac                                              20

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 66

-continued ctggccctac ctggtctttg                          20

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 67
ctagcaactc tgtcaagcaa                          20

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 68
tagagcttta cttttcatc                           20

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 69
gtttgggtgt tctgtcacag                          20

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 70
gtttggcagc tctgcagggt                          20

<210> SEQ ID NO 71
<211> LENGTH: 27
<212> TYPE: DNA
<213> ORGANISM: Artificial Sequence
<220> FEATURE:
<223> OTHER INFORMATION: Description of Artificial Sequence: Synthetic
      Oligonucleotide; Combined DNA/RNA

<400> SEQUENCE: 71
ctgaacggat cgtttcgatc ugttcag                  27

<210> SEQ ID NO 72
<211> LENGTH: 19
<212> TYPE: PRT
<213> ORGANISM: Homo sapiens
<220> FEATURE:
<223> OTHER INFORMATION: Description of Artificial Sequence: Synthetic
      Oligonucleotide

<400> SEQUENCE: 72

Gly Gln Arg Leu Pro Gln Lys Gly Asp Val Glu Met Leu Lys Gly Gly

<210> SEQ ID NO 73
<211> LENGTH: 19
<212> TYPE: PRT
<213> ORGANISM: Homo sapiens
<220> FEATURE:
<223> OTHER INFORMATION: Description of Artificial Sequence: Synthetic
      Oligonucleotide

<400> SEQUENCE: 73

Gly Gly Pro Pro Cys Gln Gly Phe Ser Gly Met Asn Arg Phe Asn Ser
 1               5                  10                  15

Arg Thr Tyr

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 74
aaacgggaac caagcaagaa                                              20

<210> SEQ ID NO 75
<211> LENGTH: 19
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 75
tgagatgtga tggtggttt                                               19

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 76
ctgaaccttc acctagcccc                                              20

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 77
gatggactca tccgatttgg                                              20

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence: Synthetic Oligonucleotide

<400> SEQUENCE: 78
ccctgccaaa cggaaacctc                                                    20

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 79
gttctctgga tgtaactcta                                                    20

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 80
agacgtagag ttacatccag                                                    20

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 81
gctctttcag gttcttctgc                                                    20

<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 82
aagaaaagag actccgaagt                                                    20

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 83
tttctcgtct ccatcttcgt                                                    20

<210> SEQ ID NO 84
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 84 gtcagcccttaggagctgtt                20

<210> SEQ ID NO 85
<211> LENGTH: 19
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 85
ggaaacagct atgaccatg                19

<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 86
gatgagaaga agcacagaag                20

<210> SEQ ID NO 87
<211> LENGTH: 24
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 87
tcatcctcgt cttttctcatc agaa                24

<210> SEQ ID NO 88
<211> LENGTH: 24
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 88
ttctgatgaa aaagacgagg atga                24

<210> SEQ ID NO 89
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 89
cattaccatc tgctttggat                20

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

```
<400> SEQUENCE: 90
aggagaagag acgcaaaacg                                                    20

<210> SEQ ID NO 91
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 91
agttcatgac tgttttggcg                                                    20

<210> SEQ ID NO 92
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 92
gtactgtaag cacggtcacc                                                    20

<210> SEQ ID NO 93
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 93
aggtgctgaa gccgatgagg                                                    20

<210> SEQ ID NO 94
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 94
tggatcactg gctttgatgg                                                    20

<210> SEQ ID NO 95
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 95
ctcgatcttg ttgatcaggt                                                    20

<210> SEQ ID NO 96
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 96
```
aggcgagccc aggcgaggcg                                              20

<210> SEQ ID NO 97
<211> LENGTH: 21
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 97
cgctcttggc aagcctgctt g                                            21

<210> SEQ ID NO 98
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 98
gtgtcagcag cctgagtgtg                                              20

<210> SEQ ID NO 99
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 99
ctccgaccca agagatgcga                                              20

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 100
gtcccaatat ggccatgaag                                              20

<210> SEQ ID NO 101
<211> LENGTH: 22
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 101
gctagataca gcggttttga gg                                           22

<210> SEQ ID NO 102
<211> LENGTH: 25
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 102
cgtcaagact gatgggaaga agagt                                              25

<210> SEQ ID NO 103
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 103
ctccatggcc cagttttcgg                                                    20

<210> SEQ ID NO 104
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 104
gtcacggcgc tgtgggagga                                                    20

<210> SEQ ID NO 105
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 105
ttgaacttgt tgtcctctgt                                                    20

<210> SEQ ID NO 106
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 106
gacctacttc taccagctgt                                                    20

<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 107
ttgaacgtga aggcctcagg                                                    20

<210> SEQ ID NO 108
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 108
ctctactact cagccaccaa                                                    20

<210> SEQ ID NO 109
<211> LENGTH: 19
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 109
tagaacttgt tgacccgga                                                 19

<210> SEQ ID NO 110
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 110
tgagactgac atcaaaatcc                                                20

<210> SEQ ID NO 111
<211> LENGTH: 19
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 111
cgaggaagta gaagcggtg                                                 19

<210> SEQ ID NO 112
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 112
cgagtgcgtc caggtgtact                                                20

<210> SEQ ID NO 113
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 113
cttccctttg tttccagggc                                                20

<210> SEQ ID NO 114
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 114
gaagggcaag cccaagtccc                                                20

-continued

<210> SEQ ID NO 115
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 115
agccatgacc agcttcagca                                                    20

<210> SEQ ID NO 116
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 116
tgctgaagct ggtcatggct                                                    20

<210> SEQ ID NO 117
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 117
cctgcagcac gccgaaggtg                                                    20

<210> SEQ ID NO 118
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 118
tccttcaagc gctccatggt                                                    20

<210> SEQ ID NO 119
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 119
tagtctgggc cacgccgtac                                                    20

<210> SEQ ID NO 120
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 120
ccggtcagta cggcgtggcc                                                    20

<210> SEQ ID NO 121
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 121
agatctccag tgccgaggct                                                 20

<210> SEQ ID NO 122
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 122
tgagctcggg tcctttccgg                                                 20

<210> SEQ ID NO 123
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 123
tccacgcagg agcagacccc                                                 20

<210> SEQ ID NO 124
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 124
tcagacggca ccatggccag                                                 20

<210> SEQ ID NO 125
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 125
cttgcccatg ggctcggggt                                                 20

<210> SEQ ID NO 126
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 126
ctctatggaa ggctcgagtg                                                 20

<210> SEQ ID NO 127

```
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 127
cggtgcttgt ccaggatgtt                                              20

<210> SEQ ID NO 128
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 128
ctgacaccta ccggctcttc                                              20

<210> SEQ ID NO 129
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 129
ggcactctct cgggctttgg                                              20

<210> SEQ ID NO 130
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 130
ggagatcaag ctttgtatgt                                              20

<210> SEQ ID NO 131
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 131
gtccttagca gcttcctcct                                              20

<210> SEQ ID NO 132
<211> LENGTH: 24
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 132
cgcctgcgga catcgtcggg cagc                                         24

<210> SEQ ID NO 133
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 133
aattaaccct cactaaaggg                                                  20

<210> SEQ ID NO 134
<211> LENGTH: 22
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 134
gtaatacgac tcactatagg gc                                               22

<210> SEQ ID NO 135
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 135
gctctttcag gttcttctgc                                                  20

<210> SEQ ID NO 136
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 136
aagaaaagag actccgaagt                                                  20

<210> SEQ ID NO 137
<211> LENGTH: 21
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 137
tgagccacag atgctgacaa a                                                21

<210> SEQ ID NO 138
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 138
gtactgtaag cacggtcacc                                                  20
```